(12) United States Patent
Kheradvar

(10) Patent No.: US 11,364,118 B2
(45) Date of Patent: Jun. 21, 2022

(54) ULTRASOUND-GUIDED DELIVERY SYSTEM FOR ACCURATE POSITIONING/REPOSITIONING OF TRANSCATHETER HEART VALVES

(71) Applicant: THE REGENTS OF THE UNIVERSITY OF CALIFORNIA, Oakland, CA (US)

(72) Inventor: Arash Kheradvar, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 197 days.

(21) Appl. No.: 16/031,916

(22) Filed: Jul. 10, 2018

(65) Prior Publication Data

US 2019/0015203 A1 Jan. 17, 2019

Related U.S. Application Data

(60) Provisional application No. 62/531,143, filed on Jul. 11, 2017.

(51) Int. Cl.
*A61F 2/24* (2006.01)
*A61B 8/12* (2006.01)
(Continued)

(52) U.S. Cl.
CPC .......... *A61F 2/2427* (2013.01); *A61B 8/0883* (2013.01); *A61B 8/12* (2013.01); *A61B 8/466* (2013.01); *A61F 2/2436* (2013.01); *A61F 2/2439* (2013.01); *A61B 5/0066* (2013.01); *A61B 5/0084* (2013.01);
(Continued)

(58) Field of Classification Search
CPC ......... A61B 8/12; A61B 8/466; A61B 8/0883; A61F 2/2436; A61F 2/2439
See application file for complete search history.

(56) References Cited

U.S. PATENT DOCUMENTS

2006/0020377 A1* 1/2006 Goetz .................... B60T 17/22
701/32.6
2006/0043191 A1* 3/2006 Patel .................. G06K 7/10722
235/462.21

(Continued)

*Primary Examiner* — Tuan V Nguyen
(74) *Attorney, Agent, or Firm* — Nguyen Tarbet LLC

(57) ABSTRACT

Some embodiments relate to Some embodiments relate to an integrated ultrasound guided delivery system for positioning or repositioning of a transcatheter heart valve including: a delivery catheter coupled to the transcatheter heart valve, and an intravascular ultrasound (IVUS) catheter operably coupled to the delivery catheter, wherein the IVUS catheter includes an ultrasound transducer tip that is aligned with a base of leaflets of the transcatheter heart valve. Also disclosed is a method for positioning or repositioning a transcatheter heart valve at a target site in a subject including: providing an integrated ultrasound guided delivery system as disclosed herein; advancing the transcatheter heart valve in the vicinity of a native valve, viewing the native valve and the target site in real-time with the IVUS catheter, and deploying the transcatheter heart valve at the target site aiming to maintain a conformal placement within the native valve annulus, thereby avoiding or minimizing paravalvular leak.

17 Claims, 37 Drawing Sheets

(51) Int. Cl.
*A61B 8/00* (2006.01)
*A61B 5/00* (2006.01)
*A61B 8/08* (2006.01)

(52) U.S. Cl.
CPC .......... *A61B 5/6852* (2013.01); *A61F 2/2418* (2013.01); *A61F 2220/0091* (2013.01)

(56) References Cited

U.S. PATENT DOCUMENTS

| | | | | |
|---|---|---|---|---|
| 2006/0259137 | A1* | 11/2006 | Artof | A61F 2/243 623/2.18 |
| 2007/0203560 | A1* | 8/2007 | Forster | A61F 2/2418 623/1.11 |
| 2013/0310923 | A1* | 11/2013 | Kheradvar | A61F 2/2439 623/2.11 |
| 2014/0107768 | A1* | 4/2014 | Venkatasubramanian | A61F 2/2496 623/2.11 |
| 2014/0228943 | A1* | 8/2014 | Stigall | A61F 2/2436 623/2.11 |
| 2014/0316518 | A1* | 10/2014 | Kheradvar | A61F 2/2418 623/2.11 |
| 2017/0086974 | A1* | 3/2017 | Lashinski | A61B 17/068 |

* cited by examiner

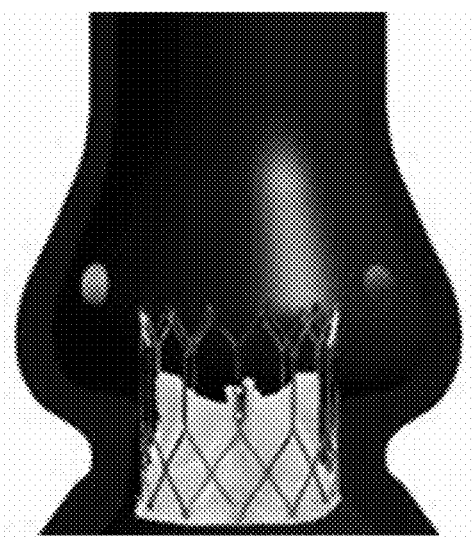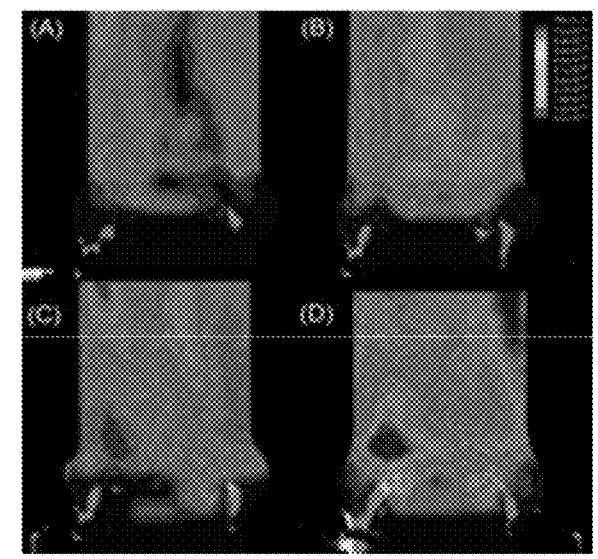
Fig. 8

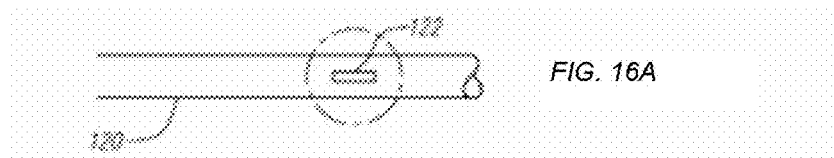
FIG. 16A
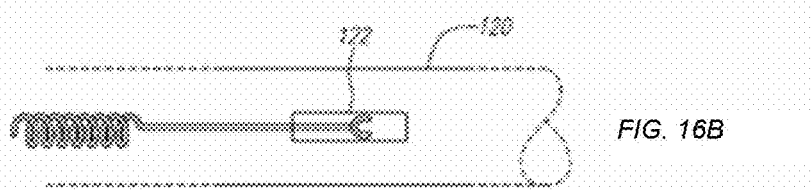
FIG. 16B
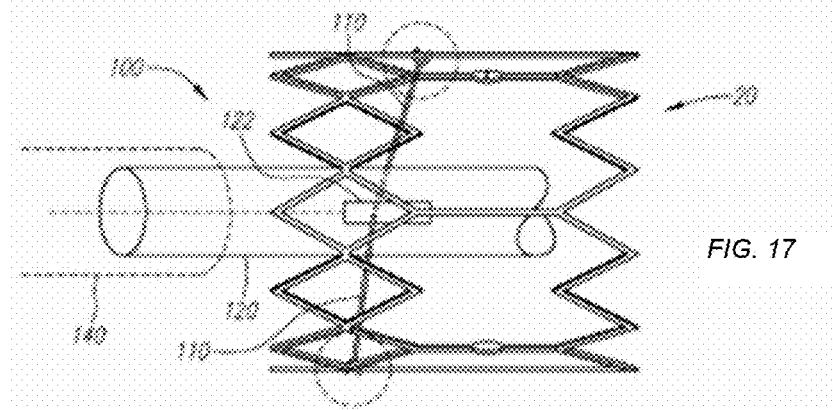
FIG. 17
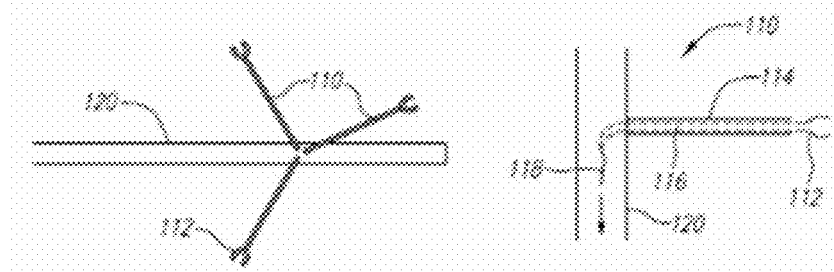
FIG. 18A
FIG. 18B

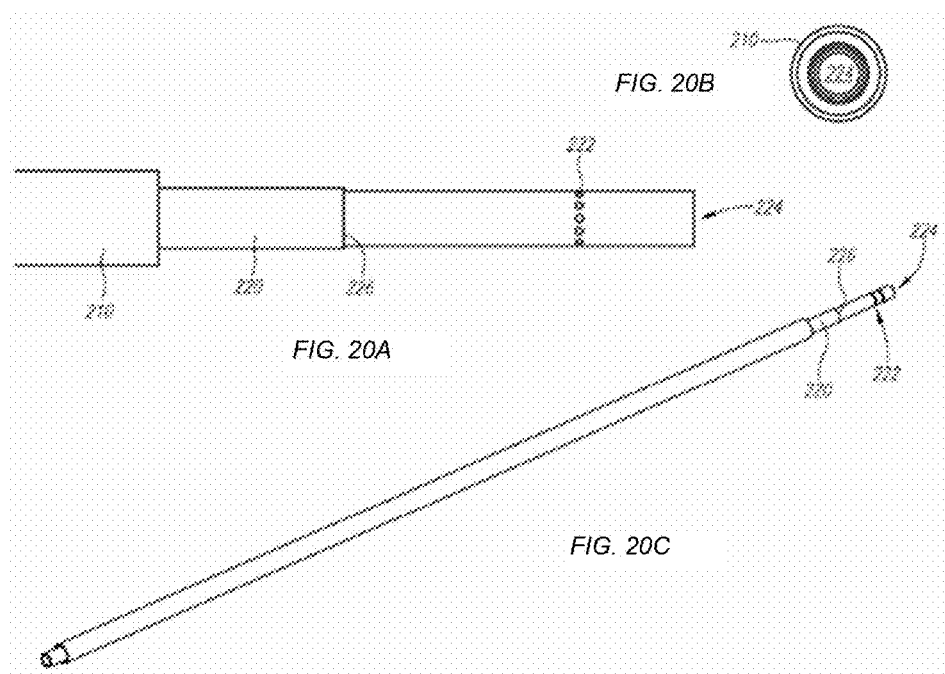

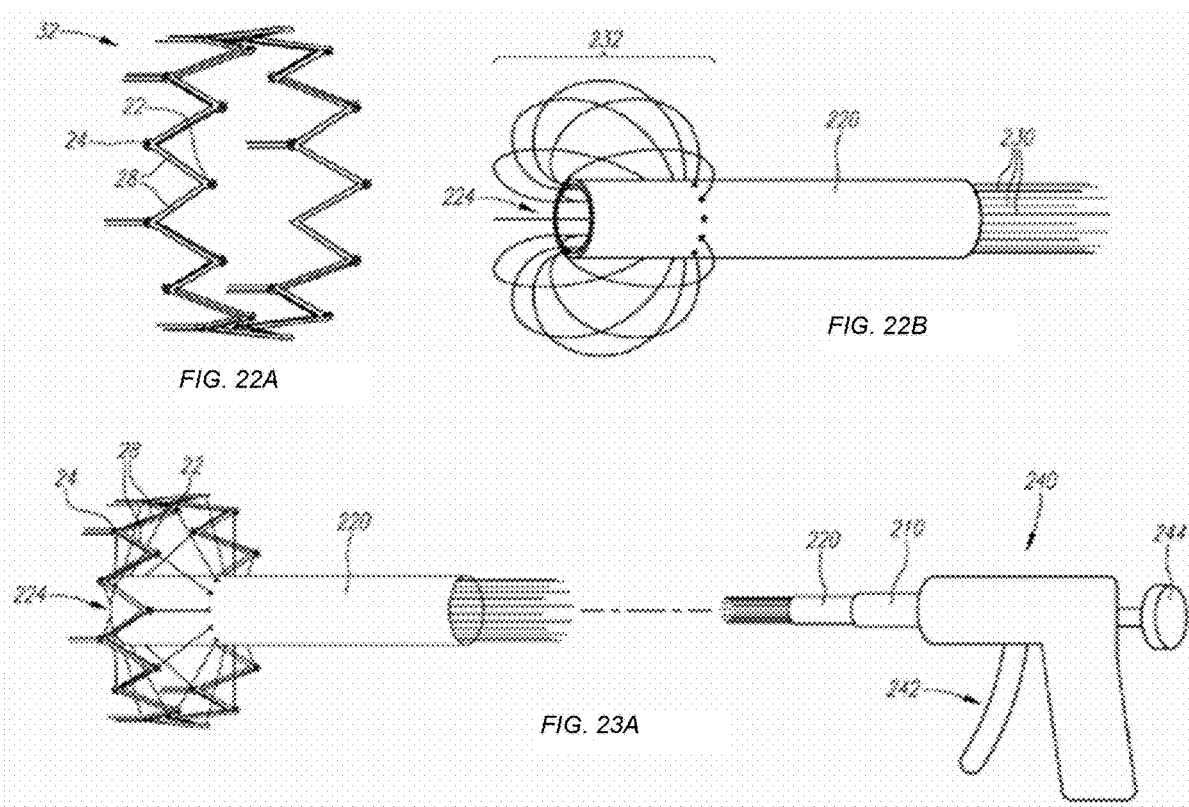

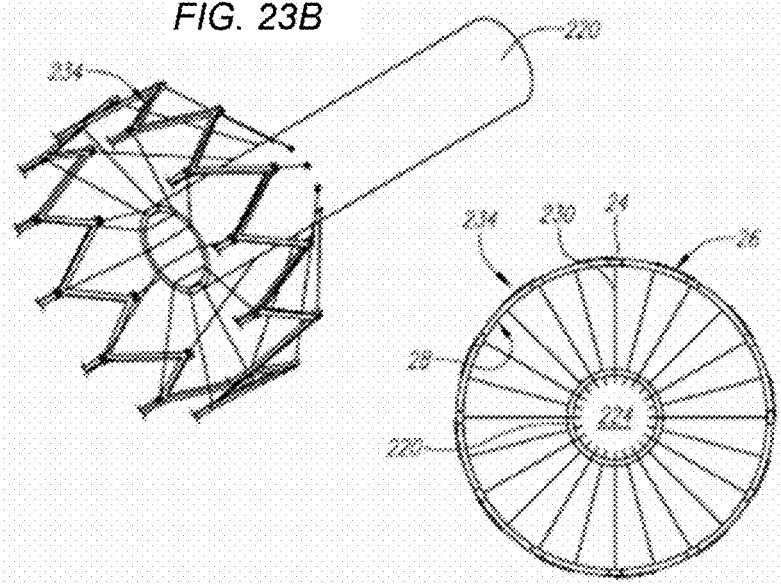
FIG. 23B
FIG. 23C
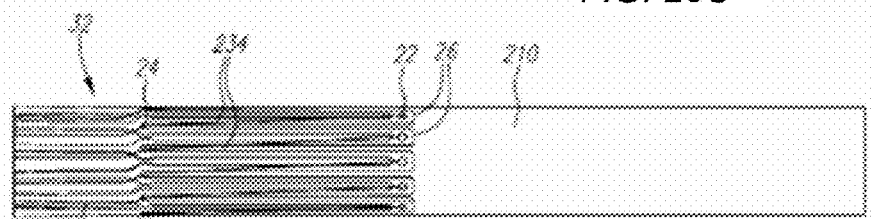
FIG. 24A
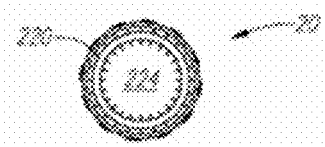
FIG. 23B

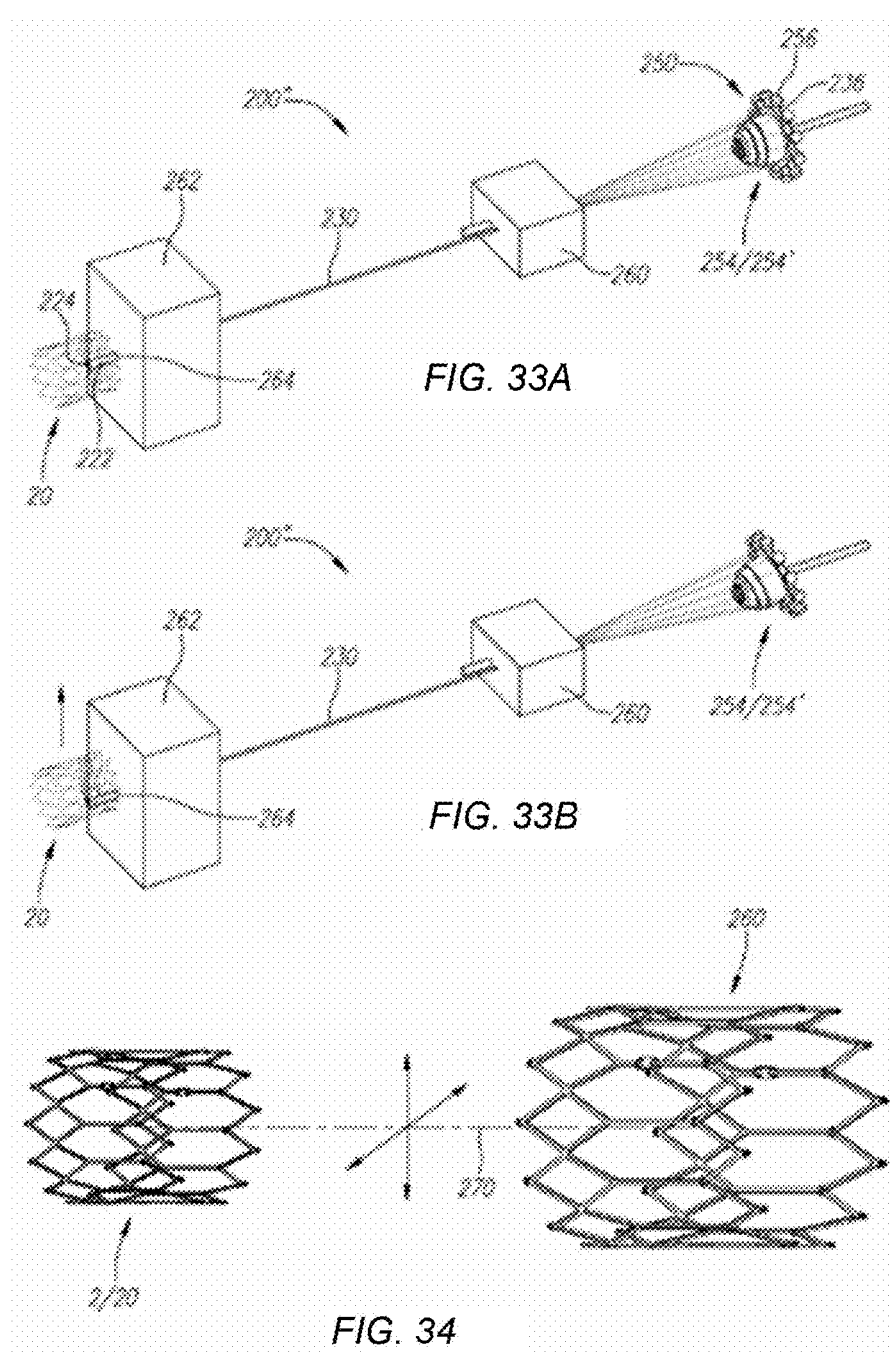

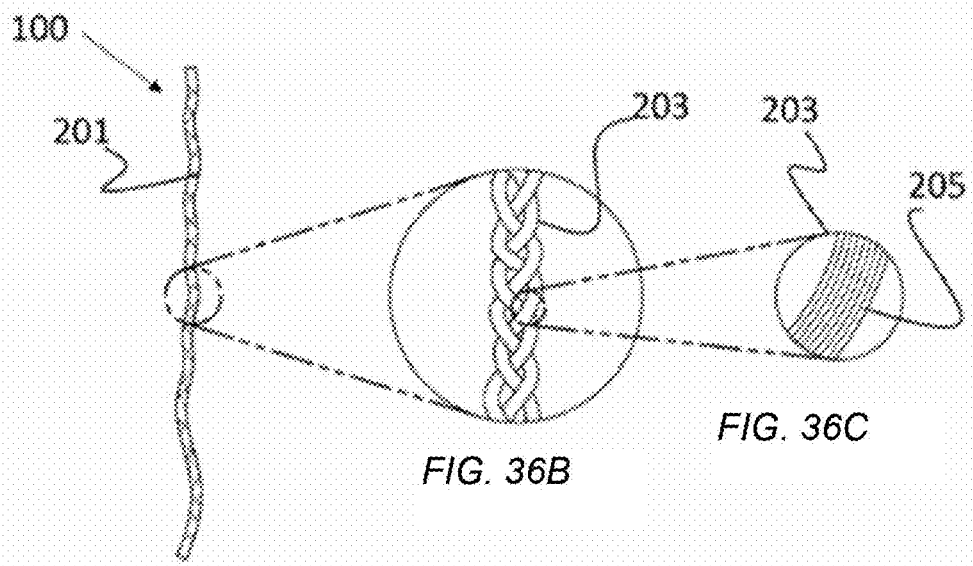
FIG. 36A
FIG. 36B
FIG. 36C
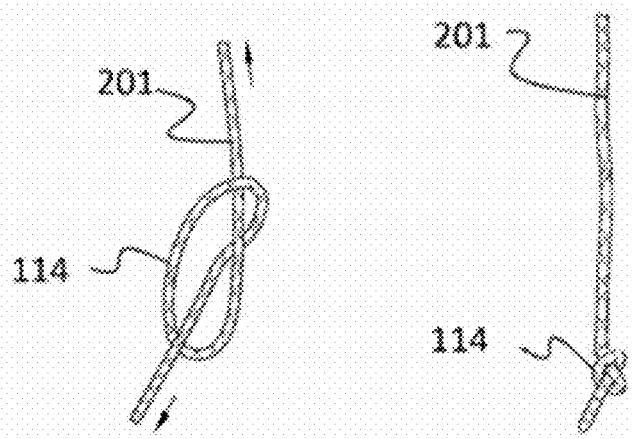
FIG. 36D
FIG. 36E

FIG. 37A-A

ULTRASOUND-GUIDED DELIVERY SYSTEM FOR ACCURATE POSITIONING/REPOSITIONING OF TRANSCATHETER HEART VALVES

STATEMENT REGARDING FEDERALLY SPONSORED R&D

This invention was made with government support under Grant Number R21 EB21513 awarded by the National Institutes of Health. The government has certain rights in the invention.

BACKGROUND

Field

A novel ultrasound-guided delivery system for implanting transcatheter heart valves is disclosed. This new technology enables accurate positioning and repositioning of the device during implantation to ensure valvular competency, and avoid paravalvular leakage and coronary ostia obstruction.

Description of the Related Art

Transcatheter aortic valve replacement (TAVR) has become an invaluable treatment option for high-risk patients who cannot undergo surgical heart valve replacement (Leon M B, et al. 2010 *The New England Journal of Medicine* 363:1597-1607; and Mack M J. 2010 *Tex Heart Inst J* 37:658-659). TAVR's introduction has been found to reduce symptoms related to severe aortic stenosis and improve patients' survival (Leon M B, et al. 2010 *The New England Journal of Medicine* 363:1597-1607; Cribier A, et al. 2002 *Circulation* 106:3006-3008; and Makkar R R, et al. 2012 *The New England Journal of Medicine* 366:1696-1704). Studies have shown that the TAVR procedure results in a 20% lower 1-year mortality when compared to standard surgical therapy (Leon M B, et al. 2010 *The New England Journal of Medicine* 363:1597-1607). Despite these results, the main challenge for a successful TAVR procedure is optimal positioning of the transcatheter aortic prosthesis (Geisbusch S, et al. 2010 *Circulation. Cardiovascular interventions* 3:531-536). Approximately 25% of TAVR failures are due to the device's being implanted abnormally low or high within the aortic root, requiring a bailout procedure to correct the implantation error (Ussia G P, et al. 2010 *Catheterization and cardiovascular interventions: Official journal of the Society for Cardiac Angiography & Interventions* 76:440-449). If valve deployment is too high within the native valve annulus or even beyond within the aorta, there is a risk of aortic injury, valvular regurgitation, and aortic embolization (FIG. 1). Valve deployment that extends too low into the ventricle can cause valvular dysfunction, heart block, regurgitation, and embolization (FIG. 1) (Thomas M, et al. 2010 *Circulation* 122:62-69; Ussia G P, et al. 2011 *Journal of the American College of Cardiology* 57:1062-1068; and Masson J-B, et al. 2009 *JACC: Cardiovascular Interventions* 2:811-820). Overall, post-deployment prosthesis embolization is due mainly to a serious error in the device's positioning (FIG. 2) (Masson J-B, et al. 2009 *JACC: Cardiovascular Interventions* 2:811-820; and Richardt D, et al. 2015 *New England Journal of Medicine* 372:1079-1081).

SUMMARY

Disclosed are embodiments that include combining intravascular ultrasound (IVUS) with a transcatheter heart valve delivery system to optimally position, repositioning or retrieve a transcatheter heart valve.

Some embodiments relate to an integrated ultrasound guided delivery system for positioning or repositioning of a transcatheter heart valve including:
a delivery catheter coupled to the transcatheter heart valve, and
an intravascular ultrasound (IVUS) catheter operably coupled to the delivery catheter, wherein the IVUS catheter includes an ultrasound transducer tip that is aligned with a base of leaflets of the transcatheter heart valve.

In some embodiments, the ultrasound transducer tip is positioned such that annular diameters of a native valve can be imaged and measured.

In some embodiments, the delivery catheter is 24 French (Fr), 22 Fr, 20 Fr, 18 Fr, 16 Fr, 14 Fr, 12 Fr or less in size.

In some embodiments, the system is additionally equipped with an optical computed tomography (OCT) sensor.

In some embodiments, the transcatheter valve is selected from the group consisting of an aortic valve, a mitral valve, a pulmonary valve, and a tricuspid valve Some embodiments relate to a method for positioning or repositioning a transcatheter heart valve at a target site in a subject including:
providing the integrated ultrasound guided delivery system as disclosed herein;
advancing the transcatheter heart valve in the vicinity of a native valve,
viewing the native valve and the target site in real-time with the IVUS catheter, and
deploying the transcatheter heart valve at the target site aiming to maintain a conformal placement within the native valve annulus, thereby avoiding or minimizing paravalvular leak.

In some embodiments, viewing the native valve further includes visualizing calcification on the native valve at the target site.

In some embodiments, the method includes approaching to reach the heart through a vascular system.

In some embodiments, the method includes approaching to reach the heart directly by poking the heart.

In some embodiments, the method includes producing a stack of cross-sectional images while retracting the IVUS catheter relative to the native valve, and tomographically combining the images to produce a three-dimensional representation of the aortic root.

In some embodiments, the the target site is viewed while the ultrasound transducer tip is positioned distally past a distal terminus of the transcatheter heart valve or wherein the target site is viewed while the ultrasound transducer tip is positioned within the transcatheter heart valve.

In some embodiments, deploying the transcatheter heart valve at the target site comprises manipulating the transcatheter heart valve based on the visualized calcification.

In some embodiments, deploying the transcatheter heart valve at the target site includes simultaneously viewing the target site and the transcatheter heart valve using the IVUS catheter.

In some embodiments, viewing the native valve and the target site includes displaying real-time images on a display, wherein the images are two-dimensional cross-sectional images or wherein the images are three-dimensional.

In some embodiments, deploying the transcatheter heart valve to the target site comprises radially expanding the transcatheter heart valve.

In some embodiments, the method further includes:
radially compressing the transcatheter heart valve;
repositioning the delivery catheter with respect to the target site while viewing the target site with the with the IVUS catheter; and
redeploying the transcatheter heart valve while viewing the transcatheter heart valve and the target site with the IVUS catheter.

In some embodiments, the IVUS catheter is rotated and moved distally or proximally while imaging.

In some embodiments, the method is performed without a second imaging modality

In some embodiments, the target site includes an aortic annulus and the transcatheter heart valve is a prosthetic aortic heart valve.

In some embodiments, deploying the transcatheter heart valve comprises positioning or repositioning the transcatheter heart valve in six degrees of freedom.

In some embodiments, the method is performed without transesophageal echocardiography (TEE).

In some embodiments, the method is performed without intracardiac echocardiography (ICE).

In some embodiments, viewing the target deployment site with the IVUS catheter includes viewing a native aortic valve and an aortic annulus straight to the front.

BRIEF DESCRIPTION OF THE DRAWINGS

FIG. 8. (Left) FOLDAVALVE position in aortic sinus and with respect to coronary ostia; (Right) Reynolds' shear stress at 4 L/min of cardiac output. The transcatheter valve's annulus was placed at (A) 5 mm, (B) 10 mm, (C) 15 mm, and (D) 20 mm below the aortic annulus; increasing the displacement results in the shear stress increasing dramatically and the flow becoming more unstable and asymmetric. The images are from Groves et al. (2014).

FIG. 16A is a detail view illustrating the delivery device sleeve of a first embodiment showing the location of one of a plurality of embedded arms.

FIG. 16B is a detail view illustrating the arm at the location in FIG. 2A connected to a spring system for controlling stent frame deployment.

FIG. 17 is a system overview illustrating the arms releasably attached to a stent frame.

FIG. 18A is a detail view illustrating the arms fully extended from the delivery apparatus and FIG. 18B is a detail view illustrating a hollow deployment arm with strings inside and a pull/push mechanism inside the guide tube or sleeve.

FIGS. 20A-20C illustrate side, end, and perspective views, respectively, of the delivery device sleeve of the second embodiment.

FIG. 22A illustrates a variation of the subject stent frame and FIG. 22B illustrates a variation of the subject delivery sleeve with associated draw line filaments.

FIGS. 23A-23C are side, perspective, and end views, respectively, illustrating the components in FIGS. 22A and 22B assembled together.

FIGS. 24A and 24B are side and end views, respectively, illustrating the same assembled components shown in a compressed state.

FIGS. 33A and 33B are photographs illustrating prototype hardware of the delivery system embodiment diagrammatically illustrated in FIGS. 18A and 18B.

FIG. 34 diagrammatically illustrates an alternative user interface for the FIGS. 18A and 18B delivery system.

FIG. 36A is an illustration of a braided suture.

FIG. 36B is an expanded view of FIG. 36A, illustrating a three-stand braided suture and strands.

FIG. 36C is an expanded view of FIG. 36B, illustrating a multiple filament structure of the strands.

FIG. 36D is an illustration of a knot, untightened.

FIG. 36E is an illustration of a knot, tightened.

FIG. 37A-A is an expanded view of FIG. 37A, illustrating a multiple filament structure of the strands.

FIG. 38B is an illustration depicting a restraining part with a hole, the braided suture through the hole, and the release line through the braided suture opening (as illustrated in FIG. 38B, the release line is larger than the hole in the restraining part, alternatively the width of the release line may be smaller than the hole where the release line is sufficiently stiff to resist being pulled into the hole).

DETAILED DESCRIPTION

Methods to Remedy Malposition in TAVR

Figure 1:
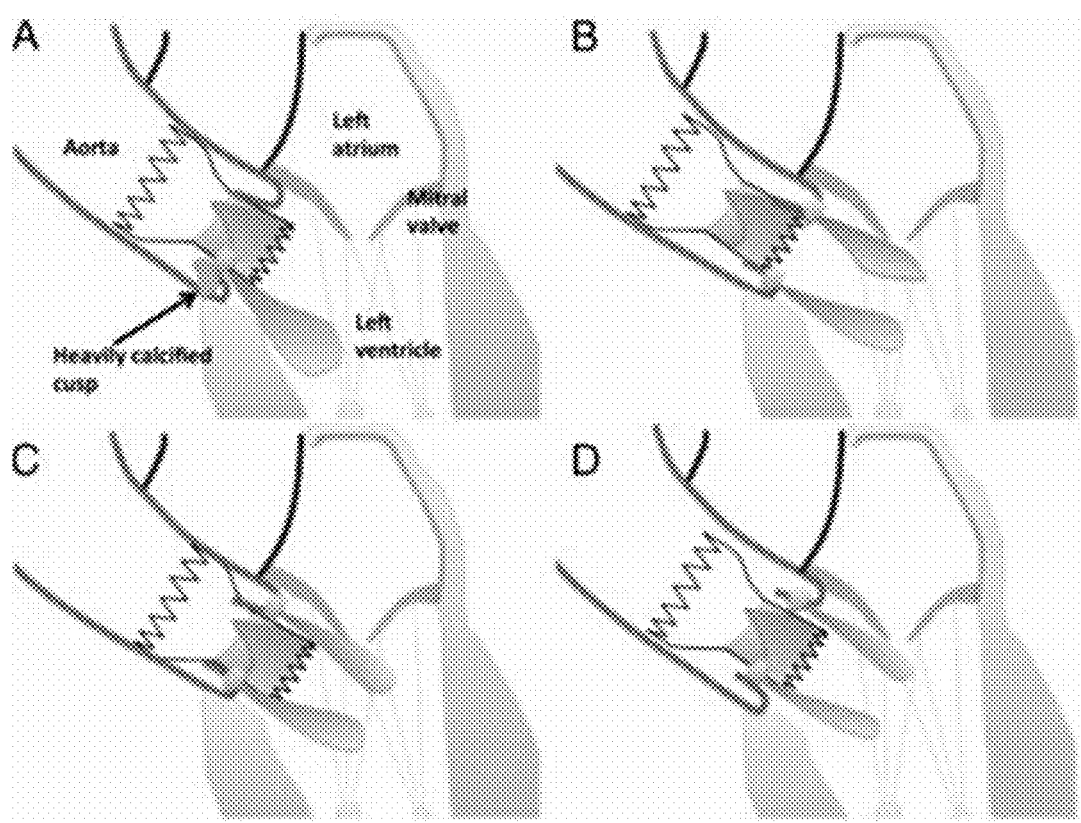
FIG. 1. Paravalvular aortic leak due to improper positioning of transcatheter aortic valve. Paravalvular leaks with consecutive peri-prosthetic aortic regurgitation result from improper positioning of the stent frame, usually caused by (A) calcifications of the annulus or the cusps of the native valve; (B) valve malposition too high; (C) or too low; (D) implantation depth of the prosthesis, and/or annulus-prosthesis-size mismatch. The image is adapted from Sinning J M, et al. (2012).
Figure 2:
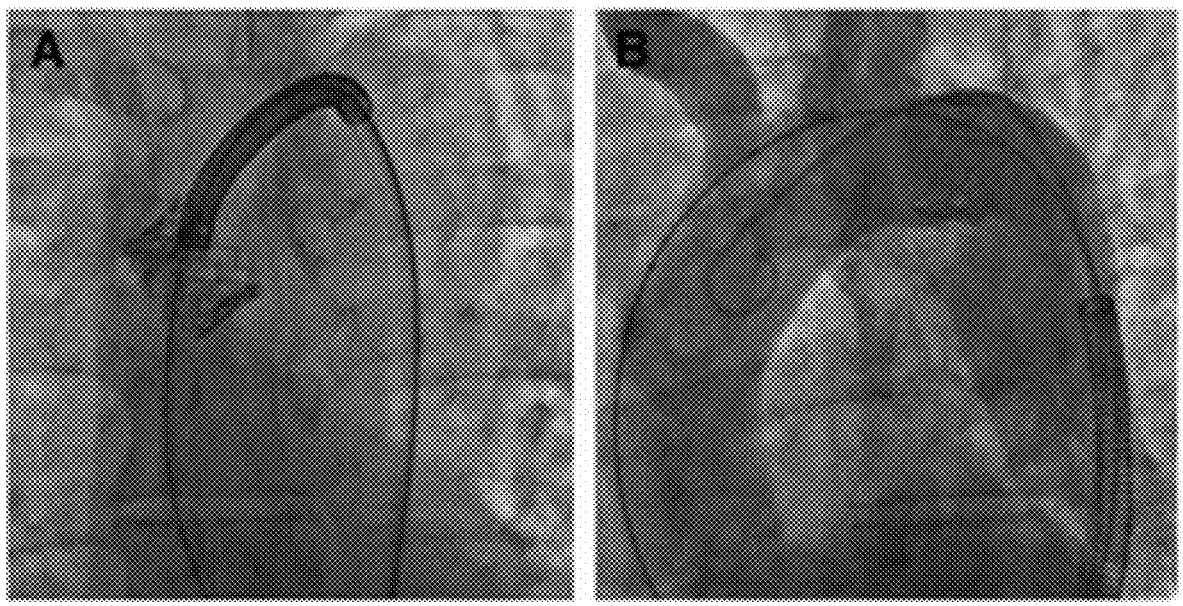
FIG. 2. (A) The embolized valve orientation is maintained by the wire position. (B) The stented valve is secured in the aorta with no detectable gradient across it. From Masson J B et al. (2009).
Figure 3:
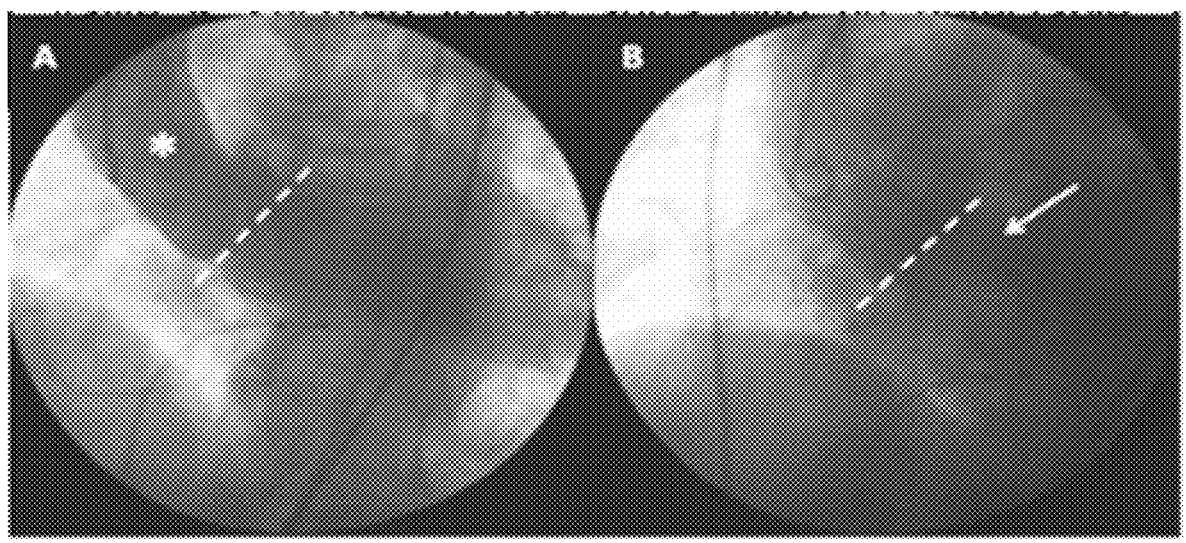
FIG. 3. (A) Angiography shows high position of CoreValve prosthesis, resulting in severe perivalvular leak. (B) Angiographic confirmation of deployment fix using a second CoreValve device, resulting in valve-in-valve. Figure from Ussia et al.

To remedy potential malposition, acceptable bailout procedures involve using a snare to reposition the valve, or deploying a second TAVR device within the first TAVR, leaving one operational valve (Giri J, et al. 2012 *Catheterization and cardiovascular interventions: official journal of the Society for Cardiac Angiography & Interventions*; Webb J G, et al. 2010 *Circulation* 121:1848-1857; and Gurvitch R, et al. 2011 *Journal of the American College of Cardiology* 58:2196-2209). The two-TAVR valve is generally referred to as "valve-in-valve" (V-in-V; FIG. 3) (Ussia G P, et al. 2010 *Catheterization and cardiovascular interventions: Official journal of the Society for Cardiac Angiography & Interventions* 76:440-449). In the worst-case scenario, surgical bailout is required to retrieve a damaged or malfunctioning TAVR device. Vin-V has become an acceptable technique to correct early implant failure (Webb J G, et al. 2010 *Circulation* 121:1848-1857; Gurvitch R, et al. 2011 *Journal of the American College of Cardiology* 58:2196-2209; and Piazza N, et al. 2009 *Catheterization and cardiovascular interven-* tions: *official journal of the Society for Cardiac Angiography & Interventions* 73:530-539). However, as the second valve compresses and deforms the first valve's leaflets, it can significantly affect the valve's hemodynamics (Groves E M, et al. 2014 *ASAIO Journal* 60:545-552). Also, intermediate and long-term consequences of V-in-V implantation have not yet been extensively studied (Ruiz C E, et al. 2008 *Catheterization and cardiovascular interventions: official journal of the Society for Cardiac Angiography & Interventions* 72:143-148; and Sarkar K, et al. 2012 *Catheterization and cardiovascular interventions: official journal of the Society for Cardiac Angiography & Interventions* 79:777-782).

It is believed that delivery catheters smaller than 15 French (Fr) provide a seemingly smooth transition and delivery (Sarkar K, et al. 2012 *Catheterization and cardiovascular interventions: official journal of the Society for Cardiac Angiography & Interventions* 79:777-782; and Thielmann M, et al. 2011 *Herz.* 36:696-704). Dissection of the ascending or descending aorta can occur due to catheter trauma, and vascular perforation can lead to retroperitoneal hemorrhage (Masson J-B, et al. 2009 *JACC: Cardiovascular Interventions* 2:811-820; and Svensson L G, et al. 2008 *Ann Thorac Surg* 86:46-54). These issues can be resolved by introducing a repositionable TAVR system deliverable equipped with an imaging modality that can convey the valve's local position within the vascular and native valvular structure.

Use of Imaging Technologies in TAVR

Imaging modalities in TAVR: Repositionability is an important option to have in case of initial malpositioning. However, an efficient imaging modality integrated into the valve's delivery system should facilitate accurate positioning and result in improved procedural success without the need to reposition. Patients suffering from highly calcified aortic valve leaflets can experience significant valvular regurgitation with a replacement valve implanted within their native valve. Therefore, in addition to the need for repositionability, accurate image guidance is a necessity for optimal positioning within a calcified native valve to minimize valvular leakage. This in turn requires on-site visualization of the root and the leaflet anatomy. Currently, TAVR procedures are simultaneously guided by X-ray fluoroscopy and transesophageal echocardiography (TEE). Incorrect valve sizing and positioning are shown to occur due to difficulties that exist in imaging the optimal view of the native valve and annulus (Rodes-Cabau J. 2010 Progress in transcatheter aortic valve implantation. *Revista espanola de cardiologia* 63:439-450). X-ray's limited 2D-projection can underestimate the aortic valve's size and shape when the imaging plane is oriented obliquely to the valve (Su J L, et al. 2009 *Optics Express* 17:19894-19901; and Elgort D R, et al. 2006 *Journal of magnetic resonance imaging: JMRI* 23:619-627). Therefore, three-dimensional imaging modalities such as CT and MRI are used for screening and follow-up in TAVR, but cannot be used for intraprocedural imaging due to their relatively slow acquisition speed (de Heer L M, et al. 2012 *Future Cardiology* 8:413-424; Buzzatti N, et al. 2012 *European journal of cardio-thoracic surgery: official journal of the European Association for Cardio-thoracic Surgery*; and Kempfert J, et al. 2012 *European journal of cardio-thoracic surgery: official journal of the European Association for Cardio-thoracic Surgery*). Furthermore, although CT and MRI can nicely visualize the aortic root and aortic arch, both modalities have difficulty imaging leaflet calcification (Koos R, et al. 2006 *Radiology* 241:76-82). Although it has been widely accepted that cross-sectional measurements of the aortic annulus using contrast CT offer the most accurate dimensions for TAVR sizing (Jilaihawi H, et al. 2012 *Journal of the American College of Cardiology* 59:1275-1286; and Willson A B, et al. 2012 *Journal of the American College of Cardiology* 59:1287-1294) precise calcium scoring remains a challenging task (Jilaihawi H, et al. 2014 *European Heart Journal—Cardiovascular Imaging* 15:1324-1332). Leaflet imaging is necessary to determine the native valve's calcification level. Despite its shortcomings, angiography is still being used for real-time assessment during TAVR procedures. For valve sizing, currently CT is the method of choice (Blasco A, et al. 2010 *Revista Española de Cardiología (English Edition)* 63:598-601; and White R A, et al. 1995 *Journal of Vascular Surgery* 21:365-374).

Applications and limitations of transesophageal echocardiography (TEE) in TAVR: Ultrasound has been used as a procedural imaging technique for valve implantation based on its real-time capabilities and non-ionizing modality. TEE has been used as an imaging tool during TAVR procedures (Moss R R, et al. 2008 *JACC. Cardiovascular imaging* 1:15-24; and Naqvi T Z. 2009 *JACC. Cardiovascular imaging* 2:1226-1237) and can visualize the aortic root and ventricular portions of the anatomy, and provide other anatomical references that may support more accurate positioning (Dumont E, et al. 2009 *The Journal of thoracic and cardiovascular surgery* 138:1022-1024; and Janosi R A, et al. 2009 *MITAT: Official journal of the Society for Minimally Invasive Therapy* 18:142-148). TEE is currently used to image leaflet calcification based on ultrasound's superior ability to resolve calcium deposits in tissues. However, TEE monitoring usually necessitates general anesthesia and endotracheal intubation (Bartel T, et al. 2015 *European Heart Journal—Cardiovascular Imaging*). TEE guidance during TAVR is based on the initial experience, and more recently there has been a decline in use of TEE for transfemoral TAVR procedures (Bartel T, et al. 2015 *European Heart Journal—Cardiovascular Imaging*). This is mainly because general anesthesia and endotracheal intubation for TAVR has increasingly been considered undesirable for transfemoral procedures. According to Pislaru et el. (Pislaru S V, et al. 2014 *Progress in Cardiovascular Diseases* 57:32-46), only a few centers consider TEE acceptable in patients undergoing conscious sedation for TAVR. TEE's other limitations in TAVR include: interference with fluoroscopic viewing, the Doppler beam's lack of coaxiality with the ascending aorta and transaortic flow, and the need for additional support staff for TEE guidance (Bartel T, et al. 2011 *Journal of the American Society of Echocardiography* 24:966-975). Further, TEE provides intermittent rather than continuous monitoring because its probe impedes fluoroscopic viewing and must be withdrawn and repositioned a few times during a TAVR procedure (Bartel T, et al. 2015 *European Heart Journal—Cardiovascular Imaging*). This limitation is more prominent during the valve deployment, as the operator prefers to have an unimpeded fluoroscopic view of the delivery system obstructed by the position of the TEE probe (Bartel T, et al. 2015 *European Heart Journal—Cardiovascular Imaging*). There is a need for a real-time imaging tool that can both visualize the cardiovascular anatomy and guide the TAVR device's placement during the implantation procedure without the limitations imposed by the use of TEE.

Applications and limitations of intracardiac echocardiography: Another use of ultrasound in TAVR procedures, intracardiac echocardiography (ICE), uses a lower-resolution transducer to visualize the entire heart within the imaging plane (Bartel T, et al. 2011 *Journal of the American Society of Echocardiography* 24:966-975). ICE provides continuous echocardiographic monitoring and can reduce TAVR's risk of complication (Bartel T, et al. 2015 *European Heart Journal—Cardiovascular Imaging*). In particular, TAVR performed under ICE guidance requires lower doses of contrast and is associated with a lower risk of acute kidney injury (Sengupta P P, et al. 2015 *JACC: Cardiovascular Imaging* 8:379-380). Two major disadvantages of ICE guidance for TAVR are the need for insertion of a second venous sheath, potential interference with the pacemaker lead needed for rapid pacing, and the risk of dislodgement (Bartel T, et al. 2015 *European Heart Journal—Cardiovascular Imaging*). Other drawbacks include the risk of provoking transient arrhythmias, a limited field of view if real-time three-dimensional (RT-3D) ICE is used, and finally the need for supplemental training of invasive and non-invasive cardiologists (Bartel T, et al. 2015 *European Heart Journal—Cardiovascular Imaging*).

While intravascular ultrasound (IVUS) has not been directly compared to CT in aortic valve imaging, it has been compared to CT in aortic imaging and guidance of aortic endograft placement; human and animal studies have shown IVUS to be as reliable as CT in measuring the aortic luminal diameter (Blasco A, et al. 2010 *Revista Española de Cardiología (English Edition)* 63:598-601; and White R A, et al. 1995 *Journal of Vascular Surgery* 21:365-374). This reliability in imaging and procedural guidance provides a basis for extending to imaging and procedures involving the aortic valve. IVUS has been a gold standard for evaluating coronary calcium burdens, to which CT scan's calcium scoring is usually compared (Okabe T, et al. 2009 *Cardiovascular Revascularization Medicine* 10:30-35; and Choi Y H, et al. 2011 *J Korean Med Sci.* 26:1052-1060).

Figure 4:
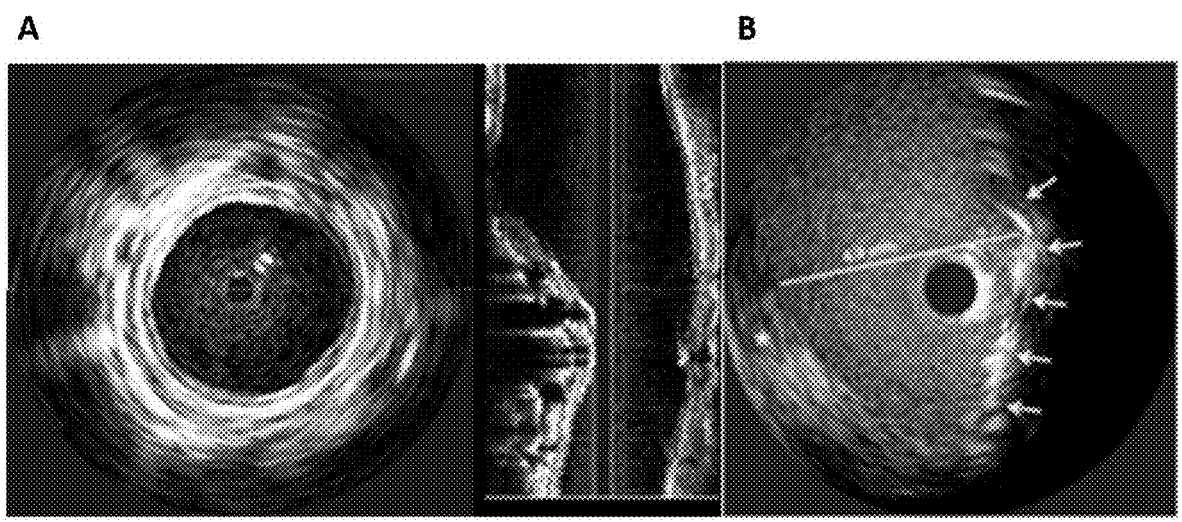
FIG. 4: (A) Intravascular ultrasound used to interrogate the distal neck of a thoracic aortic aneurysm for a fixation site of aortic endograft. Images are from Kpdonu et al. (2008); (B) IVUS image showing minimal leak diameter between the aortic wall (asterisk) and the mechanical valve ring (arrows). The image is from Avila et al. 2012.

Applications and limitations of IVUS: In addition to coronary artery assessment, IVUS has been used for full evaluation of the aorta due to its small catheter size (as small as 6 Fr; FIG. 4A) (Kpodonu J, et al. 2008 *The Annals of thoracic surgery* 86:1391-1398). In fact, despite aortic motion, vascular surgeons have called the use of aortic imaging with IVUS "essential" during aortic endografting (Beebe H G. 1997 *Journal of Endovascular Surgery* 4:111-123). IVUS has also been used to determine the optimal placement of coronary stents based on the acoustic beam's high specular reflection off stents' metal surfaces (Kawase Y, et al. 2005 *Ultrasound in medicine & biology* 31:1343-1349; and Mintz G S, et al. 2001 *Journal of the American College of Cardiology* 37:1478-1492). More recently, a case of a percutaneous aortic paraprosthetic leak closure guided by IVUS has been reported without general anesthesia (FIG. 4B) (Ávila P, et al. 2012 *Cardiovasc Interv and Ther* 27:137-139). Accordingly, the authors concluded that the use of IVUS is safe, feasible, and useful to guide percutaneous closure of paravalvular leaks (Avila P, et al. 2012 *Cardiovasc Intern and Ther* 27:137-139). Overall, IVUS's higher resolution, compared to TEE or ICE, provides detailed evaluation of the size, tortuosity, and presence of calcification (Ferrari E, et al. 2011 *European journal of cardio-thoracic surgery: official journal of the European Association for Cardio-thoracic Surgery* 40:522-524), but at the moment cannot be used simultaneously during the procedure since only one catheter (TAVR or IVUS) can occupy the aortic root region at any time-point. If used separately, the IVUS catheter can be physically damaged once the stent frame expands from crimped size to a full 21 mm or greater diameter. Therefore, it is essential to develop a TAVR delivery system with an integral IVUS component that provides an inherent real-time imaging ultrasound modality. Our current delivery system, INGENUITY, allows the valve's repositioning and retrieval to effectively mitigate implantation errors and establish optimal deployment targets within the aortic root. As it would be integrated into the delivery system, using IVUS during a TAVR procedure would involve no additional morbidity to the patient, and requires no additional sedation or mechanical ventilation. Although safe to implant, TEE mostly requires general anesthesia, is costly, and does carry the risk of devastating consequences, such as esophageal perforation, gastrointestinal bleeding, pharyngeal hematoma, and methemoglobinemia (Mathur S K and Singh P. 2009 *Indian Journal of Anaesthesia* 53:567-574; Jánosi R A, et al. 2014 *Current Cardiovascular Imaging Reports* 7:9296; Maragiannis D and Little S H. 2014 *Cardiovascular Journal* 10:172-177; and Klein A A, et al. 2014 *Anesthesia & Analgesia* 119:784-798). We believe the shortcomings of current procedural technologies should be resolved using an IVUS system incorporated into a TAVR delivery catheter.

Cost basis comparison: Compared to IVUS, TEE imposes several additional costs. To begin with, TEE requires a cardiac sonographer and an additional cardiologist to be present for the procedure, whereas with an IVUS-integrated delivery system, the physician preforming the TAVR controls the IVUS as a delivery system gadget. Use of TEE alone costs between $250 to $500 before physician fees, depending on the institution (Klein A L, et al. 2004 *Journal of the American College of Cardiology* 43:1217-1224). In most cases, then, using TEE in a TAVR procedure requires the use of mechanical ventilation and general anesthesia or at least deep sedation, which necessitates the presence of an anesthesiologist and/or a respiratory therapist, which can add between $300-$400 to the procedure (Schechter M A et al. 2012 Surgery). The direct cost of a disposable IVUS catheter for a consumer is about $600-$900 depending on the manufacturer, which can be much less if purchased wholesale to be incorporated in a TAVR delivery system.

TEE and ICE catheters are more costly than IVUS. A study that compared ICE and TEE reported that the average global hospital and physician charges related to using ICE or TEE for intraprocedural guidance are quite similar (USD 34,861±4,759 vs. USD 32,812±2,656, respectively, p=0.107) (Alboliras E T and Hijazi Z M 2004 *The American Journal of Cardiology* 94:690-692). According to Alboliras and Hijazi, In Europe, health insurance agencies usually do not cover the costs of ICE catheters, limiting its adoption there (Alboliras E T and Hijazi Z M 2004 *The American Journal of Cardiology* 94:690-692). The second component of cost extends beyond TEE and ICE; since an IVUS-integrated delivery system, as disclosed herein, improves the implantation procedure's accuracy, the chance of malpositioning should be reduced and accordingly the need for V-in-V implantation, which is currently the only transcatheter solution for a malpositioned TAV. Therefore, by eliminating the cost of the second valve to be used, the IVUS-integrated delivery systems disclosed herein should lead to a considerable cost saving.

TAVR/TMVR requires image-guidance during implantation to successfully deploy the heart valve into the correct position within the patient's aortic annulus. Current image technology uses X-Ray, CT, MRI or ultrasound to visualize the surrounding anatomy. However, only X-Ray can be used during the procedure for image guidance. X-Ray is not sufficient for visualization because it is a 2D projection of 3D anatomy that depends on the orientation angle of visualization. Currently, other imaging modalities can be used prior to the procedure and during follow-up, with the hopes that anatomical visualization can be directly correlated to the X-Ray images seen during the procedure. However, differences in contrast, resolution and artifacts can produce differing results.

A Novel Ultrasound-Guided Delivery System

This disclosure allows clinicians to image both the surrounding anatomy and the advancing catheter in real-time during the procedure. Since IVUS is a tomographic imaging modality, a 3D image of the aortic root can be produced through pull-back imaging. High-resolution IVUS is well-known for interrogating the lumen wall of vessels and has also been used to visualize metal stents in vivo. The invention can more accurately image and position the TAVR device without the use of ionizing radiation or nephrotoxic contrast agents. Furthermore, IVUS is a real-time imaging modality.

The technology disclosed herein can be used to accurately deploy a TAVR/TMVR device into a patient with greater accuracy and precision than with current procedural imaging modalities.

We have developed and tested a novel ultrasound-guided delivery system for implanting transcatheter aortic valves. This new technology enables accurate positioning and repositioning of the device during implantation to ensure valvular competency, and avoid paravalvular leakage and coronary ostia obstruction.

Within the past few years, transcatheter aortic valve replacement (TAVR) has emerged as a viable treatment option for patients with severe aortic valve stenosis (AS) who cannot tolerate standard surgical valve replacement. Two such devices are currently available in the U.S. market: CoreValve by Medtronic, Inc., and Sapien by Edwards Lifesciences Corp. The recent PARTNER clinical trial provided data on the use of TAVR as an effective alternative to the standard medical therapy for aortic valve replacement in patients with major contraindications to surgery. Despite this positive outlook, implantation failures continue to occur; reports indicate that 5-25% of all TAVR procedures fail. Of that number, Ussia et al. (2010) reported that more than 25% of failed transcatheter procedures are due to the valve's being implanted abnormally low or high within the aortic root. Valve migration, which takes place in 22% of implant failures, causes additional procedural failures. These procedural failures require additional surgical intervention or a second TAVR device to be deployed within the first (valve-in-valve). Moreover, with self-expanding TAVR frames, precise positioning of the catheter prior to deployment can be difficult due to the frame's "prosthesis jump," either superior, into the Sinuses of Valsalva, or inferior, into the left ventricle, leading either to immediate procedural failure or the valve's failure to operate correctly.

Currently, real-time fluoroscopy imaging is insufficient to accurately identify optimal deployment areas in the aortic anatomy. Improper implantation may result in obstruction of coronary ostia by the implanted valve, or debris dislocation in a highly calcified valve. Transesophageal Echocardiography (TEE) has been investigated as a complementary imaging modality for TAVR procedures; however, TEE operates at a lower resolution, can result in significant complications, and is uncomfortable for most patients. Additionally, TEE requires general anesthesia during the procedure, and a push is being made to perform TAVR solely under conscious sedation, which would not allow the use of TEE over long time periods. This project aims to combine intravascular ultrasound (IVUS), which has been used successfully to optimally position coronary artery stents, with our repositioning/retrievable delivery catheter for TAVR procedure. The IVUS assists in accurate imaging of the aortic annulus and root, allowing for an improved TAVR implantation procedure compared to conventional TEE-guided procedures. We accomplish the following specific aims within this award's two-year duration:

We disclose the design and construction of an integrated ultrasound-guided delivery system for accurate positioning/repositioning of transcatheter aortic valves.

A 3D tomographic modality, has been previously used to interrogate the aorta. IVUS imaging allows accurate cross-sectional and 3D-computed views of the surrounding heart valve anatomy co-registered with the delivery catheter position. The IVUS-guided delivery system allows accurate positioning of prosthetic valves, mitigates implantation errors, and improves the effectiveness of positioning transcatheter heart valves.

We demonstrate the clinical feasibility of IVUS-guided valve implantation by delivering the valves in a sheep model (within a previously-implanted calcified polymeric aortic valve) and testing its functionality. The procedure's outcome variables are then to commonly-practiced TEE-guided implantation procedures.

An animal study is useful to test the feasibility and improvement in procedural success of using IVUS to guide in vivo implantation of transcatheter valves. We recently developed a calcified polymeric valve that is be surgically implanted first in the sheep to replicate a native calcified aortic valve. We then implant a FOLDAVALVE transcatheter valve within the calcified valve with the proposed IVUS-equipped delivery system and with a regular delivery system under TEE guidance. The endpoints to be examined and compared are the severity of paravalvular and transvalvular leak, visibility of coronary ostia, length of ascending aorta, occurrence of conduction abnormalities, stroke, and presence of ischemia. A FOLDAVALVE TAVR system can be used. However, any TAVR system can be equipped with an IVUS-guided system.

Internal catheters usually have their outside diameters measured in French sizes. The French catheter scale or "French units" (Fr) is commonly used to measure the outside diameter of needles as well as catheters. 1 "French" or "Fr" is equivalent to 0.33 mm=0.013"=$\frac{1}{77}$" of diameter. The size in French units is roughly equal to the circumference of the catheter in millimeters. A 14 to 16 French is typically used on most adults. Larger catheters of 22 French may be used for patients with hematuria or clots. Pediatric French sizes range from 3 to 14.

Figure 5:
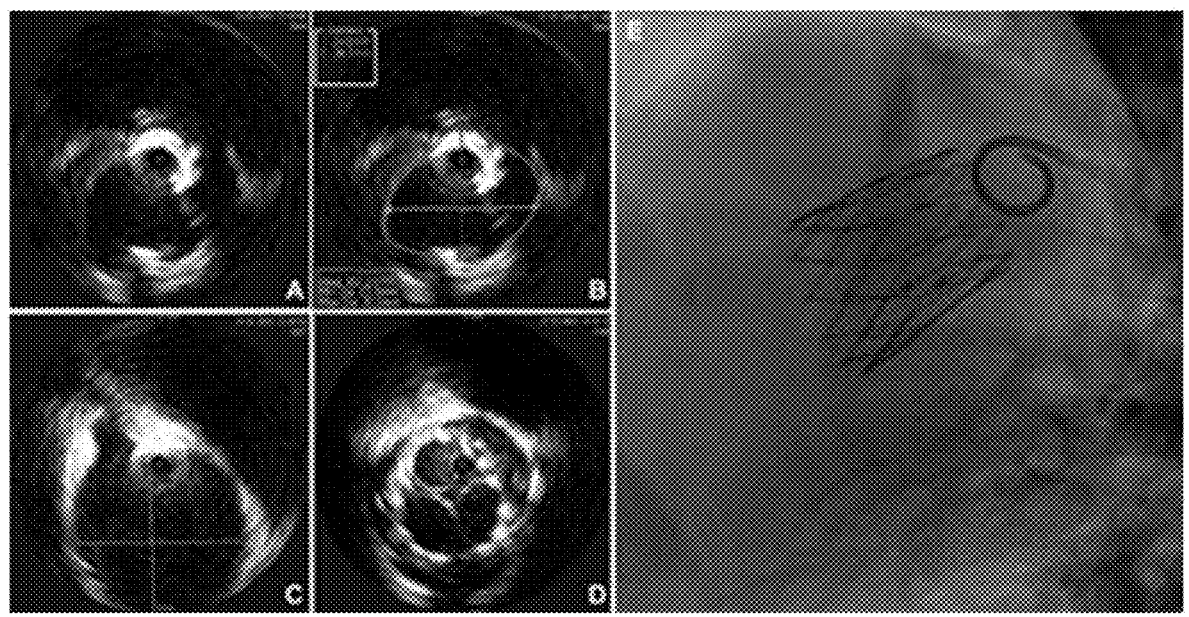
FIG. 5. Aortic Valve Ultrasound (AVUS) Pre and Post Transcatheter Aortic Valve Implantation (A) Aortic valve ultrasound (AVUS) of the aortic annulus; (B) Annulus area, and minimum and maximum annular diameters; (C) AVUS showing the ostium of the right coronary artery; (D) AVUS at prosthetic valve-level post-TAVI with a Medtronic CoreValve prosthesis (Medtronic, Minneapolis, Minn.); (E) fluoroscopic image of the FOLDAVALVE implanted at the aortic root. Images A-D are adapted from Roy D A et al. (2013), and image E is adapted from Kheradvar et al. (2015).

Specific Features (1) Accurate positioning of transcatheter heart valves is a major concern in interventional cardiology that has yet to be properly addressed. Currently, navigation of the stented aortic valve is based on fluoroscopic images that only visualize the LV aortic junction from a side view without a trace of the native valve (FIG. 5E) (Kheradvar A, et al. 2015 *Euro Intervention* 11(5):591-596). IVUS allows the native valve to be visualized with the ability to locally measure valve annular diameters (FIG. 5A-D) (Roy D A, et al. 2013 *JACC: Cardiovascular Interventions* 6:634-635). Since axial positioning of the stent is important in TAVR, it is necessary to examine the stent's placement within the native aortic valve. The IVUS-integrated delivery catheter uniquely allows the interventionalist to precisely position the transcatheter valve within the native valve while viewing the native valve and its annulus straight to the front.

(2) An IVUS integrated delivery system can locally visualize the calcified spots on the native aortic valve and navigate the valve deployment accurately to maintain a circular cross-section, avoiding paravalvular leak.

(3) The INGENUITY delivery catheter we have developed and that is be equipped with IVUS provides repositioning in six degrees-of-freedom and even works when the valve is fully formed. INGENUITY also allows retrieval if the implantation is unsuccessful (Kheradvar A, et al. 2015 *EuroIntervention* 10:pii: 20141002-20141001). Its size is under 14 French (Fr) catheter, which is the smallest among all current delivery systems. The abilities to fully reposition and retrieve a fully-deployed valve are among this system's unique characteristics, which do not yet exist in any commercially available TAVR systems.

Figure 6:
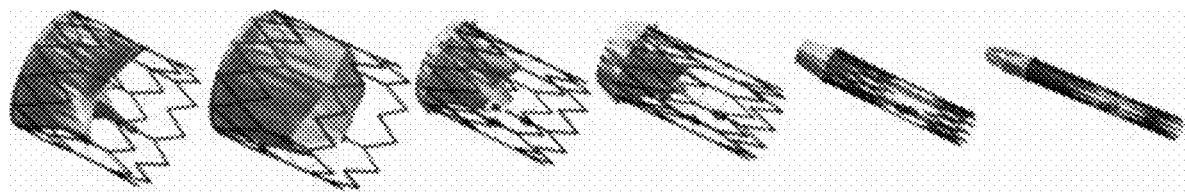
FIG. 6: FOLDAVALVE percutaneous aortic valve developed at Kheradvar Lab. The 25 mm diameter frame can be collapsed to ~14 Fr delivery size, allowing ease of access compared to larger TAVR catheters. Adapted from Kheradvar, et al., EuroIntervention (2015).
Figure 7:
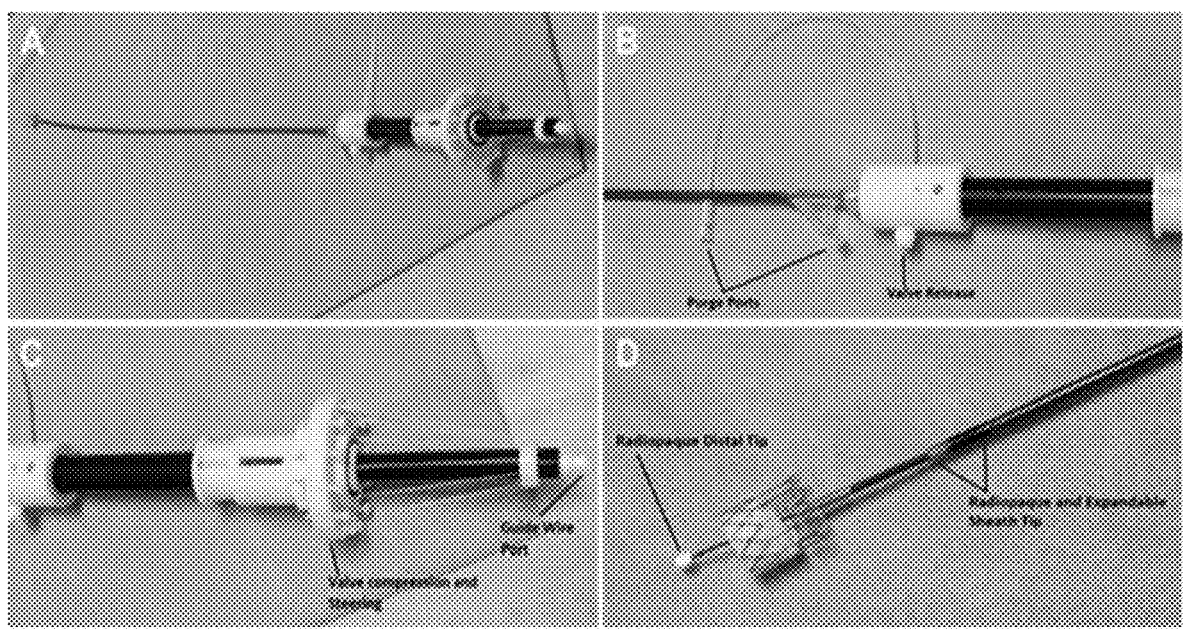
FIG. 7. The INGENUITY delivery system is pictured here. Panel A shows the INGENUITY system attached to FOLDAVALVE. Panel B shows the valve release and purge ports. Panel C illustrates the handle with its controlling force fibers that help to reposition, recapture, and release the valve. Panel D shows the distal end of the catheter and how FOLDAVALVE is attached to it. Adapted from Kheradvar, et al. (2015).

FOLDAVALVE transcatheter aortic valve system: We previously developed FOLDAVALVE (Kheradvar A, et al. 2015 *EuroIntervention* 10:pii: 20141002-20141001; U.S. Pat. No. 8,133,270; and Kheradvar A, et al. 2014 *Annals of Biomedical Engineering*, pages 1-14) a transcatheter aortic valve deliverable with a ~14 Fr delivery system, with a repositioning option and retrieval ability. FOLDAVALVE is composed of a self-expanding Nitinol stent and bovine pericardial leaflets. When crimped, the leaflets are folded outside of the frame; during deployment they are pulled into the expanding stent using a drawstring mechanism. Formation of the trileaflet valve occurs simultaneously with the stent's expansion (FIG. 6). These design features allow the valve's leaflets to be spared from damage that occurs during stent crimping and valve delivery. During implantation, the valve is fully repositionable and retrievable through the INGENUITY delivery system, which allows for six degrees of freedom in valve positioning/repositioning and has been used for transfemoral implantation (FIG. 7).

FOLDAVALVE's working prototypes have been built and tested in sheep to demonstrate its repositioning capacity in vivo (Kheradvar A, et al. 2015 *Euro Intervention* 11(5):591-596). FIG. 7 depicts a 25 mm diameter stent frame snared on its distal end using an assembly of surgical sutures. We have planned the proposed project based on the FOLDAVALVE concept due to its direct availability to us. However, upon development, the technology can be incorporated into any available TAVR delivery system, including Edwards' Sapien family, Medtronic's CoreValve, and others. Since the stent's axial positioning is crucial in TAVR, it is necessary to examine changes that may occur due to too high or too low positioning within the aortic annulus. In a series of in vitro experiments we showed that improper TAVR positioning leads to negative consequences for transvalvular flow, abnormal aortic wall stress, and mal-perfusion of the coronary arteries (Groves E M, et al. 1992 ASAIO journal (American Society for Artificial Internal Organs). These experiments deployed FOLDAVALVE within a bioprosthetic aortic valve (Biocor™, St. Jude Medical, St. Paul, Minn.) within a heart flow simulator at the Kheradvar lab. By visualizing the main jet at various stages of the heart cycle along with the circulation within the sinuses, we found that proper positioning of the stented valve within the bioprosthetic valve is crucial to get sufficient flow to the Valsalva (FIG. 8) (Groves E M, et al. 2014 *ASAIO Journal* 60:545-552).

Figure 9:
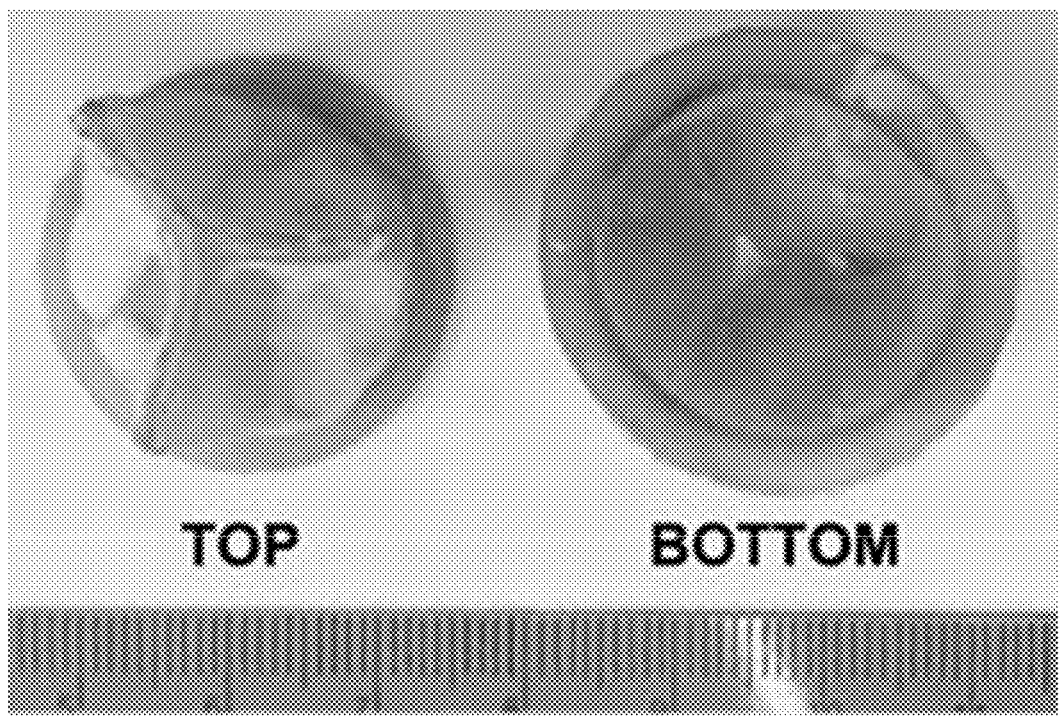
FIG. 9. 21 mm Calcified polymeric heart valve made according to shape—and position of the calcified inclusions—of a naturally calcified aortic valve. The valve is made of polyurethane combined with hydroxyapatite powder. The valve leaflets share similar material properties (e.g., bending stiffness, elastic modulus) to a natural calcific aortic valve.

Calcified polymeric heart valve: Currently there is no large animal model with natural calcified heart valve, and lack of such an animal model makes research and development studies of cardiovascular devices very difficult. Many devices, such as transcatheter heart valve technologies, must be implanted at a calcified heart valve in animals. Because such an animal model does not exist, all current heart valve systems have been tested only in animals with normal valves. To properly test our IVUS-equipped delivery system, we developed—for the first time—a fully biocompatible polymeric heart valve with calcium appetite inclusions immersed in it (FIG. 9).

Figure 10:
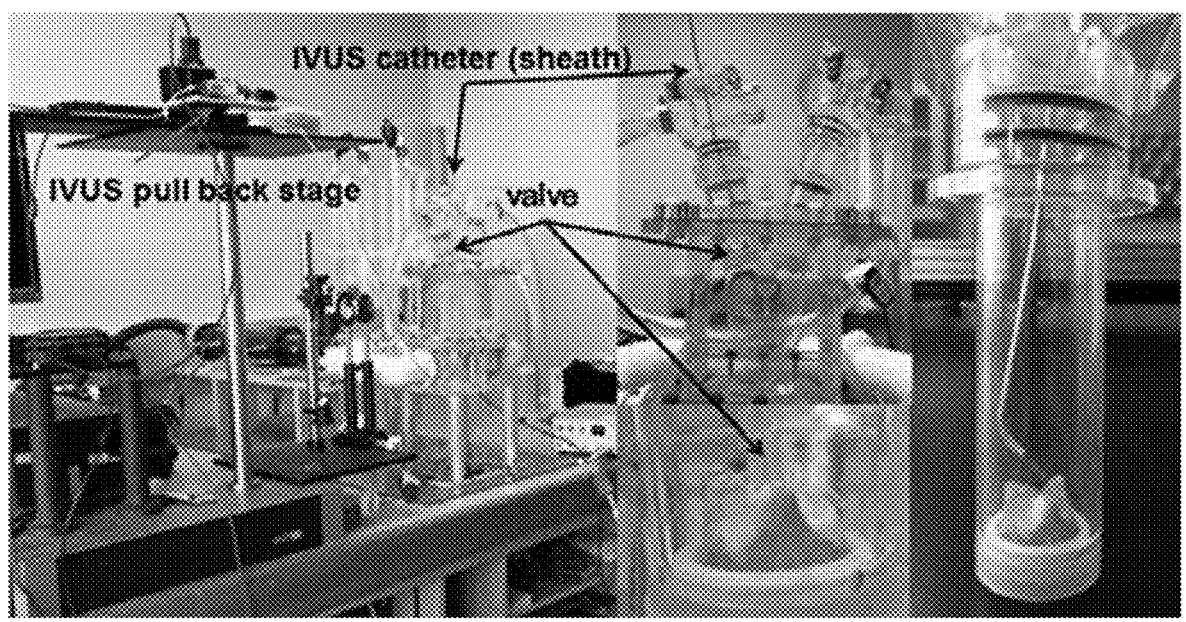
FIG. 10. The figure shows the experimental setup to image the calcified leaflet using an IVUS. The IVUS is guided through an IVUS sheath, which is inside a sealed catheter. The valve is a polymeric valve with a model of a calcification on the leaflet. The IVUS is placed over the leaflet to acquire the scans. The IVUS pull-back stage controls the IVUS, including its rotation.
Figure 11:
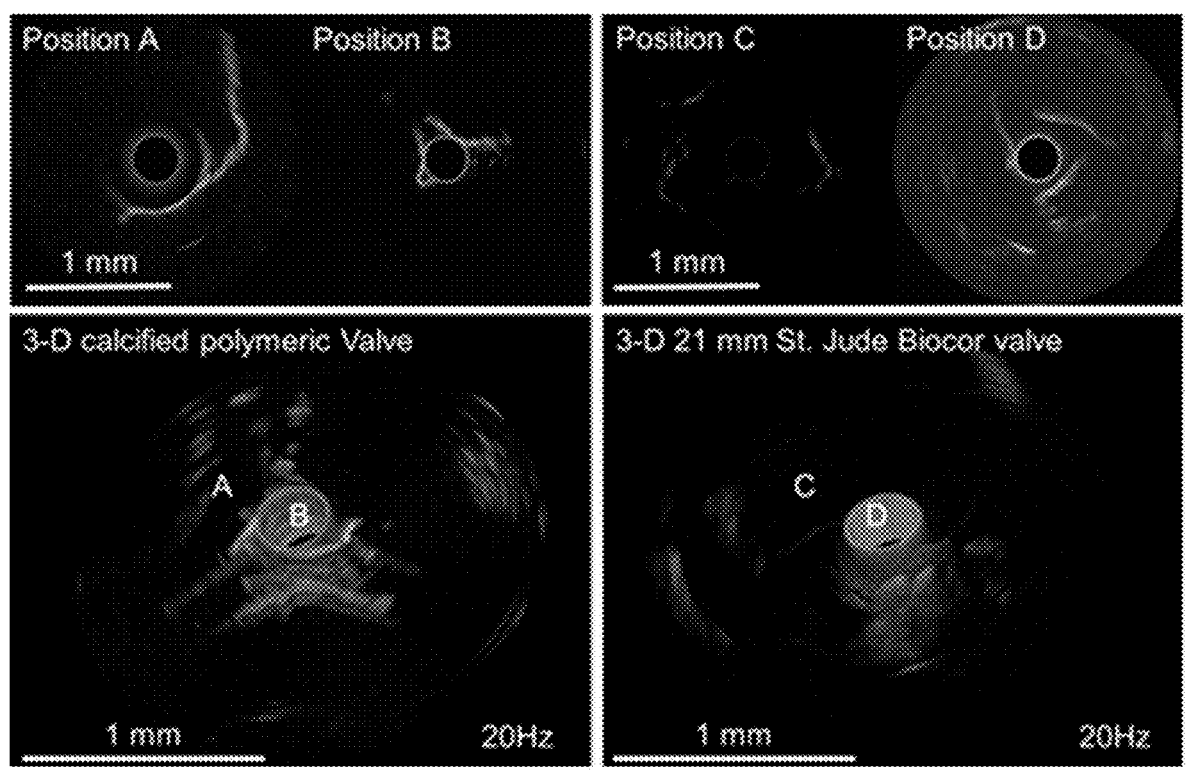
FIG. 11. Intravascular ultrasound (IVUS) imaging of 21 mm calcified polymeric and SJM Biocor™ valves. The right panels show IVUS images on a 21 mm non-calcified SJM Biocor™ valve in 2D (Top) and in 3D (Bottom). The left panels show IVUS images of 21 mm calcified polymeric valve (FIG. 11) in 2D (Top) and in 3D (Bottom). The size and position of the calcified inclusions are clearly shown.

Visualizing heart valves with IVUS: To test IVUS' ability to visualize the heart valve and identify the location of the calcified inclusions, we compared a 21 mm polymeric calcified valve (FIG. 9) to a clinical-quality St. Jude 21 mm Biocor™ aortic valve in a previously validated heart flow simulator (FIG. 10) (Falahatpisheh A and Kheradvar 2012 *European Journal of Mechanics—B/Fluids* 35:2-8). Each experiment placed the valve at the aortic position in the heart flow simulator. The IVUS was given access to the valve by passing its catheter sheet from a Plexiglas tube distal to the valve, as shown in FIG. 10. The aortic valve was dynamically scanned at a heart rate of 70 bpm. 2D and 3D scans were performed. A high-frequency single-element IVUS catheter (40 MHz Atlantis SR Pro™ imaging catheter, Boston Scientific, Inc.), with element size around 0.5 mm, was used. The imaging sheath and catheter were guided by an introducer with the end angled at ~135 degrees, and placed over the valve surface. To obtain real-time images of the valve, the ultrasound beam was rotated at 20 Hz, allowing 20 images per second to be captured. Once the IVUS catheter gradually pulled back at 50 µm/step, a stack of transverse images was obtained and longitudinal cross-sections of the valves were examined. The ultrasound signals were acquired by a 250 MHz DAQ board and post-processed by a Matlab-based program for 2-D cross-sectional imaging and 3-D volume. IVUS images demonstrated the valves' general structure, including lumen size, leaflet thickness, and location of the calcified inclusions on the calcified polymeric valve (FIG. 11).

We disclose the development and testing of an IVUS-guided delivery system and comparison of its efficacy with conventional TEE-guided implantation.

We disclose the design and construction of an integrated ultrasound-guided delivery system for accurate positioning/repositioning of transcatheter aortic valves.

IVUS imaging, a 3D tomographic modality, has been previously used to interrogate the aorta. IVUS allows accurate cross-sectional and 3D-computed views of the surrounding heart valve anatomy co-registered with the delivery catheter position. The IVUS-guided delivery system allows accurate positioning of prosthetic valves, mitigates implantation errors, and improves the effectiveness of positioning transcatheter heart valves.

Figure 12:
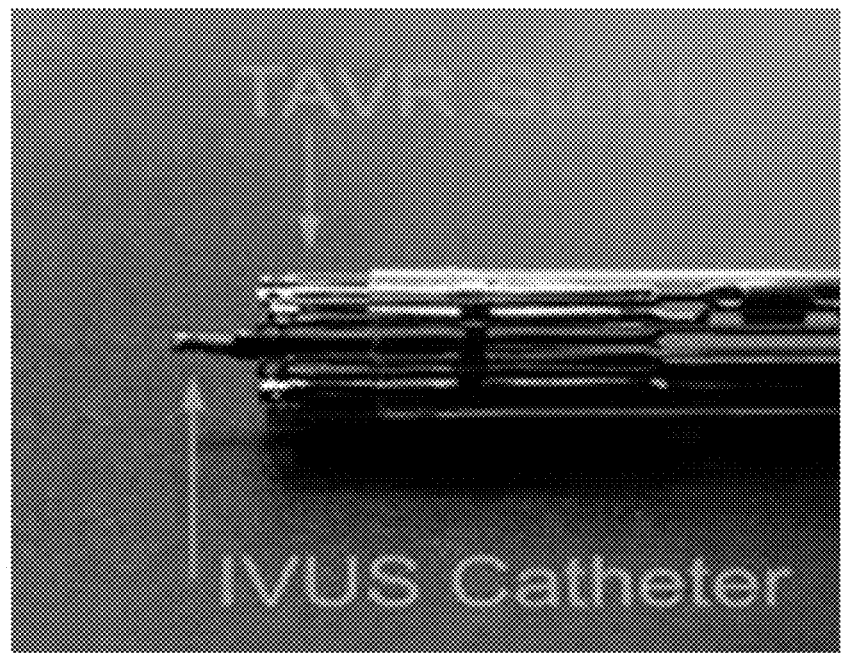
FIG. 12: Photograph of proximal end of a TAVR stent compressed to 4.3 mm diameter (13 Fr). An Atlantis SR Pro, IVUS transducer (Boston Scientific, Natick, Mass.) is placed through the center for sizing purposes.

Design and integration of an IVUS system into the valve delivery catheter: Integrating an off-the-shelf intravascular ultrasound catheter within the TAVR delivery catheter allows high-resolution imaging of the stent frame and surrounding anatomy, which is superior to current angiography methods while providing real-time visualization during the procedure. IVUS produces a 3D tomographic image through a pullback technique that acquires a stack of cross-sectional images. For example, we integrate either a Revolution™ IVUS catheter (Volcano Corporation, San Diego, Calif.) or an Atlantis SR Pro™ imaging catheter (Boston Scientific, Inc., Maple Groves, Minn.) into our TAVR delivery system (FIG. 7). These commercial off-the-shelf IVUS catheters have a maximum diameter of 3.6 Fr, and operate at a center frequency of 40-45 MHz and with peak rotational speed of 50 Hz. The IVUS system can be modified and integrated into the existing free space at the center of our TAVR stent crimped at 13 Fr (FIG. 12). This addition does not increase the delivery system's size given the IVUS catheter's small diameter compared to the TAVR stent. Adjustments can be made to the IVUS to achieve optimal performance.

Visualizing the positioning: According to previous studies on optimal stent placement, the stent's distal boundary should sit between 4 and 20 mm below the aortic annulus (Kahlert P, et al. 2012 *Journal of cardiovascular magnetic resonance: official journal of the Society for Cardiovascular Magnetic Resonance* 14:21; and Kapadia S R, et al. 2010 *Current problems in cardiology* 35:228-276). Studies using the IVUS-guided delivery system can be performed in a silicone model of the aortic root from the heart-flow simulator developed in our laboratory (Falahatpisheh A and Kheradvar 2012 *European Journal of Mechanics—B/Fluids* 35:2-8). Using the IVUS-guided delivery system, 3D image pullback can be obtained beginning from the bottom of the aortic root upward past the sinuses of Valsalva. The image pullback produces a stack of cross-sectional images, which can be tomographically combined to produce a three-dimensional representation of the aortic root, similar to FIG. 11. The data is collected using a standard IVUS acquisition system with images exported to MATLAB for offline processing.

Integration of the IVUS control system to the TAVR delivery handle: Our TAVR delivery catheter's handle can be modified (FIG. 7) to control the IVUS system. The IVUS-guided delivery system can be designed to match the stent, allowing for a temporary but firm connection during implantation. The FOLDAVALVE's superelastic stent allows deployment from 4.30 mm to 25.00 mm in diameter. The use of an assembly of fibers for controlled stent deployment is a solution we found to work well (FIG. 7). This technology allows the valve to be repositioned and retrieved under 14 Fr delivery catheters. Control of the IVUS system, which is currently computer-based, enables remote operation, multiple control devices, and custom viewing options. However, the delivery systems for transcatheter heart valves are handheld and controlled by the interventionalist adjacent to the patient. It is beneficial to integrate both control systems such that they do not negatively interfere with each other while the IVUS system guides the interventionalist to accurately position the stented valve. This problem can be addressed with the use of a simple wireless module on the TAVR delivery handle that allows remote control of the computer-based IVUS. This combined delivery system provides full control over the valve's delivery and implantation while guided by the IVUS.

Figure 13:
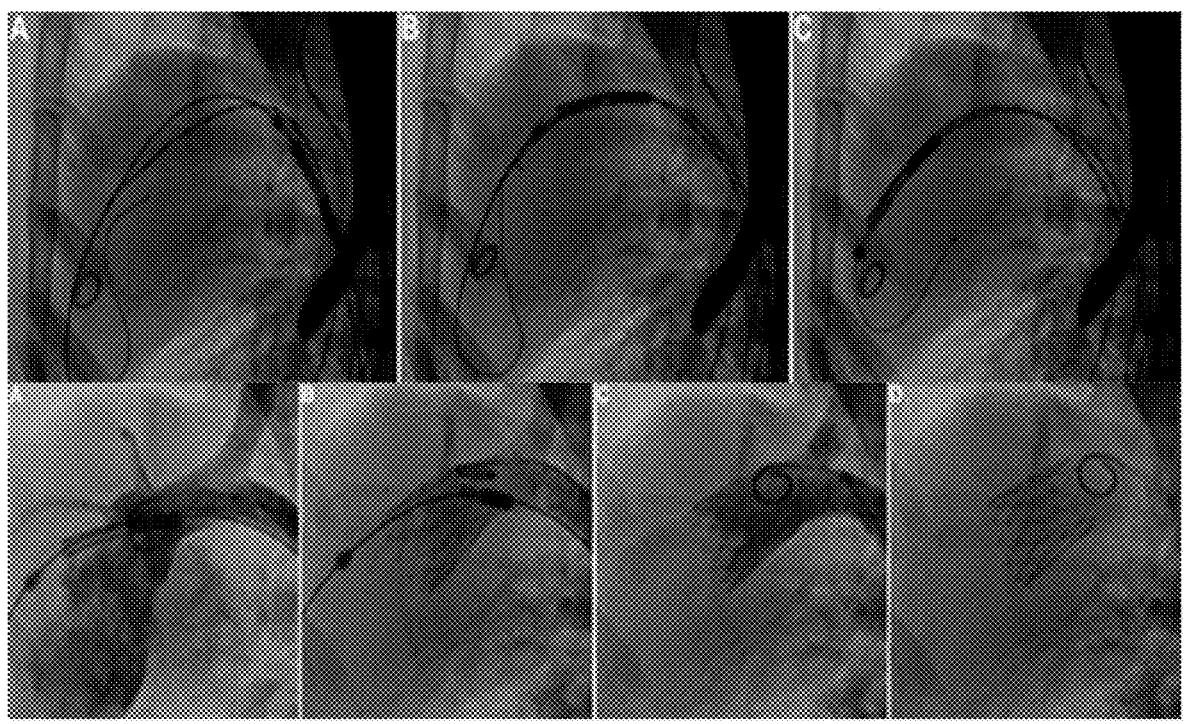
FIG. 13: The top raw shows how FOLDAVALVE is being easily passed over the aortic arch and into the left ventricular cavity immediately before staged deployment and positioning in the aortic root. The bottom row shows FOLDAVALVE being pulled back into the aortic root and positioned properly from left to right.

Prototype and testing of the integrated TAVR and IVUS delivery catheter in vitro: Our prototype consists of the IVUS transducer tip aligned with the base of the folded valve leaflets. Since FOLDAVALVE's leaflets unfold from an upside-down position, they do not obstruct the IVUS transducer during catheter positioning (FIGS. 6 and 13). The sheath for TAVR delivery and the guidewires from the IVUS transducer runs through the catheter's lumen and toward the catheter's base. The catheter base interfaces with the ultrasound acquisition hardware to allow manipulation of TAVR deployment. To test the delivery prototype's functionality, we deploy FOLDAVALVE within a properly-sized calcified aortic valve (similar to FIG. 9) under the now-integrated IVUS image guidance in the silicone model of the aortic root (FIG. 10). Physiological waveforms of the cardiac cycle are applied to imitate different conditions for the LV, as previously described (Kheradvar A and Gharib M. 2009 *Ann Biomed Eng* 37:1-13; Kheradvar A, et al. 2006 *ASAIO J* 52:34-38; and Kheradvar A, et al. 2007 *ASAIO J.* 53:8-16). The procedural outcome of IVUS-guided TAVR are compared with echocardiographic-guided TAVR, using a GE Vivid E9 system, in our heart flow simulator. Severity of paravalvular and transvalvular leakage are measured for each m and compared to each other.

We demonstrate the clinical feasibility of IVUS-guided valve implantation by delivering the valves in a sheep model (within a previously-implanted calcified polymeric aortic valve) and testing its functionality. The procedure's outcome variables are compared to commonly-practiced TEE-guided implantation procedures.

An animal study is used to test the feasibility and improving procedural success by using IVUS to guide in vivo implantation of transcatheter valves. We have developed a calcified polymeric valve that is surgically implanted first in sheep to replicate a native calcified aortic valve. We implant a FOLDAVALVE transcatheter valve within the calcified valve with the IVUS-equipped delivery system and with a regular delivery system under TEE guidance. The endpoints compared are the severity of paravalvular and transvalvular leak, visibility of coronary ostia, length of ascending aorta, occurrence of conduction abnormalities, stroke, and presence of ischemia. We use FOLDAVALVE TAVR system as an example. Calcified polymeric valves are surgically implanted in sheep prior to transcatheter intervention. Calcified valves of similar shape can be used. FIG. 13 shows FOLDAVALVE implantation steps in sheep (Kheradvar A, et al. 2015 *Euro Intervention* 11(5):591-596).

Statistical Analysis: A total of 14 sheep are used (7 to be used for IVUS-guided [group 1] and 7 for conventional TEE-guided implantation [group 2]). To compare the two implantation methods, we consider the following variable outcomes: (1) Severity of paravalvular leakage, (2) severity of transvalvular leakage, (3) visibility of coronary ostia, (4) length of ascending aorta, (5) occurrence of conduction abnormalities, (6) stroke, and (7) presence of ischemia represented by ST-elevation. Parameters 1-4 are continuous and parameters 5-7 are binary variables. Differences between two unpaired groups are evaluated using t-tests or Mann-Whitney U tests. All the p-values are two sided, and a 5% type I error level is used. Prior to fitting the statistical model for each aim, summary and graphical analysis are performed to ensure data quality and check model assumptions. For example, the data are examined to check normality assumption and, as needed, data transformation (e.g., Box-Cox transformation) is used. Alternatively, if necessary, the nonparametric Mann-Whitney-Wilcoxon and Kruskal-Wallis methods can be used for unadjusted analyses.

Completion of the animal study is followed by euthanasia and explant of the heart to inspect the deployed prosthesis and its implantation position, and to assess coronary ostia. The results from the IVUS-guided animals are compared to those that underwent the TEE-guided procedure.

The IVUS-guided implantation results in more accurate positioning of the valves and thus optimal valve performance. In some embodiments, we can implant the transcatheter valves immediately after the open-heart procedure for surgical implantation of the calcified valve. Since FOLDAVALVE does not require pacing, we can proceed with TAVR immediately following surgical implantation.

Systems, Devices and Methods

Example embodiments are described herein with respect to the systems, devices, and/or methods, including Examples 2 and 3.

Embodiments may include or utilize a prosthetic heart valve. This prosthetic heart valve can be structured or configured in various ways. Example embodiments of the valve include all embodiments of prosthetic valves described and/or shown in Examples 2 and 3. Example embodiments of the valve also include all prosthetic valves described or referred to include but are not limited to the FOLDAVALVE, which is shown and described with respect to, for example, FIGS. 6, 7, 8, and 12 and in FIGS. 15A-15F of Example 2.

Embodiments may also include or utilize a delivery device (e.g., a catheter). The delivery device can be structured or configured in various ways. Example embodiments of the delivery device include all embodiments of delivery devices described in Example 2 and/or Example 3. Example embodiments of the delivery device include all embodiments of delivery devices referred to as the INGENUITY delivery catheter, which is shown and described with respect to, for example, in FIG. 7.

The delivery device can be configured to radially expand the valve for deployment and/or redeployment in the target delivery site. The delivery device can also be configured to radially contract or compress the valve, such as with the use of multiple filaments, to assist in repositioning and/or recapturing the valve. The delivery device can be used in all steps of the delivery process, which can include advancement through the vasculature to a target delivery site (e.g., the aortic root), positioning of the valve with respect to the target delivery site, deployment of the valve (e.g., by radial expansion), recapture of the valve (e.g., by partial are full radial compression), repositioning of the valve with respect to the target delivery site, redeployment of the valve, and/or withdrawal of the device. These steps can be performed as many times as necessary to obtain the desired orientation and placement within the vasculature.

During any and all steps of the delivery process (e.g., advancement, positioning, capture, recapture, repositioning, redeployment, withdrawal, etc.) an intravascular ultrasound (IVUS) imaging device can be used to obtain image data of the target delivery site, the valve, and/or the delivery device. An ultrasound imaging device can include one or more imaging elements (e.g., transducers) coupled with an elongate shaft that are together slidably movable with respect to the delivery device. Example embodiments of the ultrasound imaging device are described in Example 2 (e.g., with respect to FIGS. 30A and 30B and elsewhere) and with respect to FIGS. 11 and 12 (e.g., the Atlantic SR Pro imaging catheter, the Revolution IVUS catheter, etc.) and elsewhere).

The one or more imaging elements can emit and/or receive ultrasound signals and produce one or more output signals that are usable to generate images of the target deployment site, the valve, and/or the delivery device. For example, the one or more output signals can be transferred from the one or more imaging elements along the elongate shaft (e.g., by an electrical conductive path) to one or more image processing and/or graphics rendering devices that can render image data suitable for display to a medical professional on a screen or monitor. The imaging and display processes can occur in real time such that minimal delay (e.g., less than one second) between capture of the ultrasound image data and display is perceived by the medical professional. The image processing and/or graphics rendering devices can include one or more processors and one or more non-transitory memories on which is stored one or more instructions for processing the data output from the one or more imaging elements to generate image data suitable for viewing on a display communicatively coupled with the image processing and/or graphics rendering devices.

The images displayed to the medical professional can be two dimensional cross-sectional images (e.g., radial or longitudinal) and/or three dimensional images (e.g., showing surface contours). In some embodiments, the one or more imaging elements are rotated to capture a 360° radial cross-sectional view, and in other embodiments the one or more imaging elements are positioned with a 360° field of view such that no rotation is needed to capture a 360° radial cross-sectional view. The one or more imaging elements can be moved proximally and/or distally (e.g., a longitudinally) to obtain radial cross-sectional images at various positions along the length of the aortic root. These images taken at various positions can then be combined to render a three-dimensional image of a longitudinal span of the aortic root. In all embodiments, images obtained by the ultrasound imaging device can depict the native valve's general structure, including lumen size, leaflet position and thickness, and location of calcified inclusions to the extent present in the native valve or in a calcified artificial valve already implanted therein.

Example embodiments of methods of delivering the valve with the assistance of IVUS imaging are described herein, and these methods can be performed with the example embodiments of a heart valve, a delivery device, and an ultrasound imaging device described herein. An ultrasound imaging device can slide through an inner lumen of the delivery device and through the interior region of the valve as shown in FIG. 30B of Example 2 and in FIG. 12. The one or more imaging elements can image only the target delivery site (e.g., the aortic root) by positioning the one or more imaging elements distal to the distal termini of the valve and the delivery device, as shown in FIG. 30B of Example 2 and FIG. 12. The one or more imaging elements can image the target delivery site and the valve when positioned within the interior region of the valve at a location between the proximal terminus and the distal terminus of the valve (a position proximal to that shown in FIG. 30B of Example 2 and in FIG. 12). Translation of the one or more imaging elements can occur by slidably moving the ultrasound imaging device with respect to the delivery device and the valve. Thus by altering the position of the ultrasound imaging device different views can be obtained at any desired time such as during any and all of the steps of the delivery process (e.g., advancement, positioning, capture, recapture, repositioning, redeployment, withdrawal, etc.). The medical professional can continuously obtain images at discrete positions of the one or more imaging elements and/or while moving the one or more imaging elements proximally and/or distally during any and all steps of the delivery process (e.g., advancement, positioning, capture, recapture, repositioning, redeployment, withdrawal, etc.).

Example embodiments of a prosthetic heart valve delivery system can include a heart valve, a delivery device, and an ultrasound imaging device. Embodiments of the system allow the native valve to be visualized with the ability to locally measure valve annular diameters (see, e.g., FIGS. 5A-D). Since axial positioning of the valve is important in TAVR, it highly desirable to examine the valve's placement within the native aortic valve. The system allows the interventionalist to precisely position the valve within the native valve while viewing the native valve and its annulus straight to the front. For example, with a transfemoral approach the interventionalist will have an end-on view (downstream looking upstream) of the outflow face of the aortic valve once passing the aortic arch. With a transapical approach from the left ventricle, the interventionalist will have the opposite end-on view (upstream looking downstream) of the inflow face of the aortic valve.

The system can locally visualize the calcified spots on the native aortic valve and navigate the valve deployment accurately to maintain a circular cross-section, avoiding paravalvular leaks. The delivery device allows repositioning of the valve in six degrees-of-freedom in various states of contraction and even when fully expanded. In some embodiments, the maximum diameter of the system is 14 French (Fr) or less.

In all embodiments described herein, any and all steps of the delivery process (e.g., advancement, positioning, capture, recapture, repositioning, redeployment, withdrawal, etc.) can be accomplished using only a single imaging modality, which is an ultrasound imaging device, and with no other (secondary) imaging modality or device. For example, any and all steps of the delivery process can be performed without transesophageal echocardiography (TEE), any and all steps of the delivery process can be performed without intracardiac echocardiography (ICE), any and all steps of the delivery process can be performed without computed tomography (CT), any and all steps of the delivery process can be performed without magnetic resonance imaging (MRI), any and all steps of the delivery process can be performed without X-ray, and any and all steps of the delivery process can be performed without fluoroscopy.

For the avoidance of doubt, all embodiments of delivery of a prosthetic heart valve with the assistance of ultrasound imaging can be performed with a CoreValve provided by Medtronic, Inc., and/or a Sapien valve provided by Edwards Lifesciences Corp.

By way of a brief summary and review, the example embodiments described herein enable accurate positioning and repositioning of the device during implantation to ensure valvular competency, and avoid paravalvular leakage and coronary ostia obstruction. TAVR/TMVR currently requires image-guidance during implantation to successfully deploy the heart valve into the correct position within the patient's aortic annulus. Current image technology uses X-Ray, CT, MRI or ultrasound to visualize the surrounding anatomy. However, only X-Ray can be used during the procedure for image guidance. X-Ray is not sufficient for visualization because it is a 2D projection of 3D anatomy that depends on the orientation angle of visualization. Currently, other imaging modalities can be used prior to the procedure and during follow-up, with the hopes that anatomical visualization can be directly correlated to the X-Ray images seen during the procedure. However, differences in contrast, resolution and artifacts can produce differing results. The example embodiments allow clinicians to image both the surrounding anatomy and the advancing catheter in real-time during the procedure. Since IVUS is a tomographic imaging modality, a 3D image of the aortic root can be produced through pull-back imaging. High-resolution IVUS is well-known for interrogating the lumen wall of vessels and has also been used to visualize metal stents in vivo. The example embodiments can more accurately image and position the TAVR device without the use of ionizing radiation or nephrotoxic contrast agents. Furthermore, IVUS is a real-time imaging modality.

Computer program instructions for carrying out operations in accordance with the described subject matter may be written in any combination of one or more programming languages, including an object oriented programming language such as Java, JavaScript, Smalltalk, C++, C #, Transact-SQL, XML, PHP or the like and conventional procedural programming languages, such as the "C" programming language or similar programming languages. The program instructions may execute entirely on the user's computing device, partly on the user's computing device, as a stand-alone software package, partly on the user's computing device and partly on a remote computing device or entirely on the remote computing device or server.

Example 1

Intravascular Ultrasound for Detection of Valvular Calcification

As the aging society advances, aortic valve calcification and aortic valve stenosis (AS) is becoming one of central issues to be solved in cardiovascular field. Thanks to the rapid progress of medical device research and development, a considerable number of AS cases can be treated by transcatheter aortic valve replacement (TAVR). Despite such expansion of TAVR, clinical concerns associated with TAVR procedures still remain. In particular, stroke or other embolic complications due to detachment of tissue-derived debris are still the most serious problems to be solved. Intravascular ultrasound (IVUS) has been established as useful imaging modality in coronary intervention, but its usefulness for TAVR procedure has not been validated. In this study, with the aim of exploring the practicality of IVUS guide for TAVR, we used IVUS to characterize the morphology of calcified valves leaflets in vitro.

Methods

Figure 14:
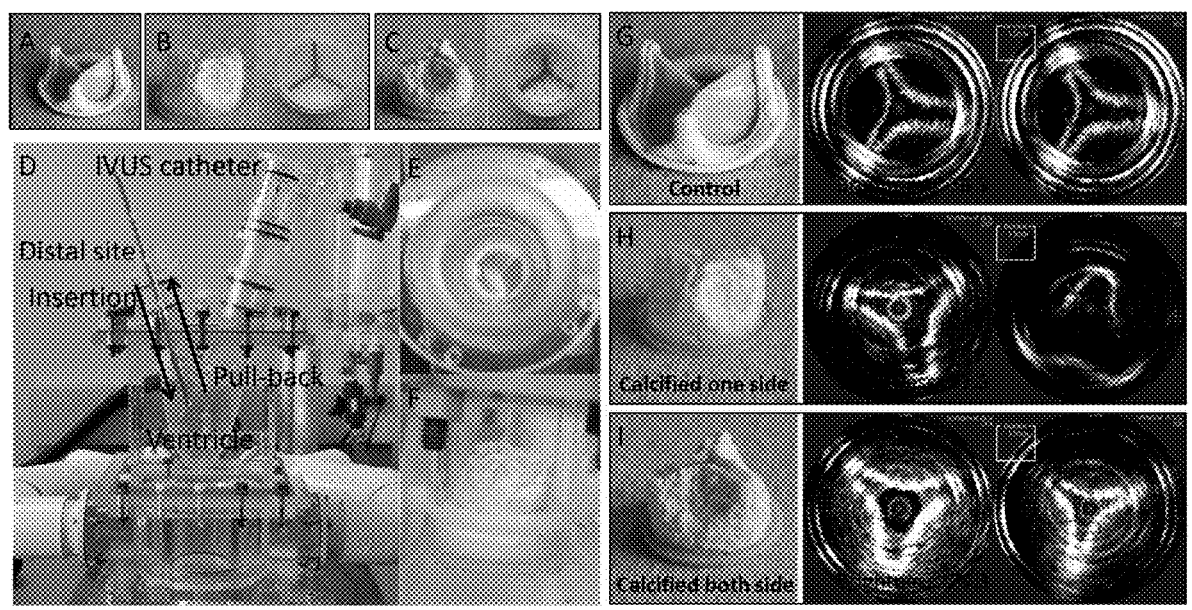
FIG. 14. Heart flow simulator and components. (A) Control valve; (B) polymeric valve with moderate calcification on aorta-side leaflets; (C) polymeric valve with severe calcification on both sides of leaflets; (D) Heart flow simulator; (E and F) each aortic valve was placed in aortic valve position; (G) control non-calcified valve; (H) polymeric valve with moderate calcification on aortic-side leaflet; and (I) severely-calcified polymeric valve.
Figures 15A, 15B, 15C, 15D, 15E, 15F:
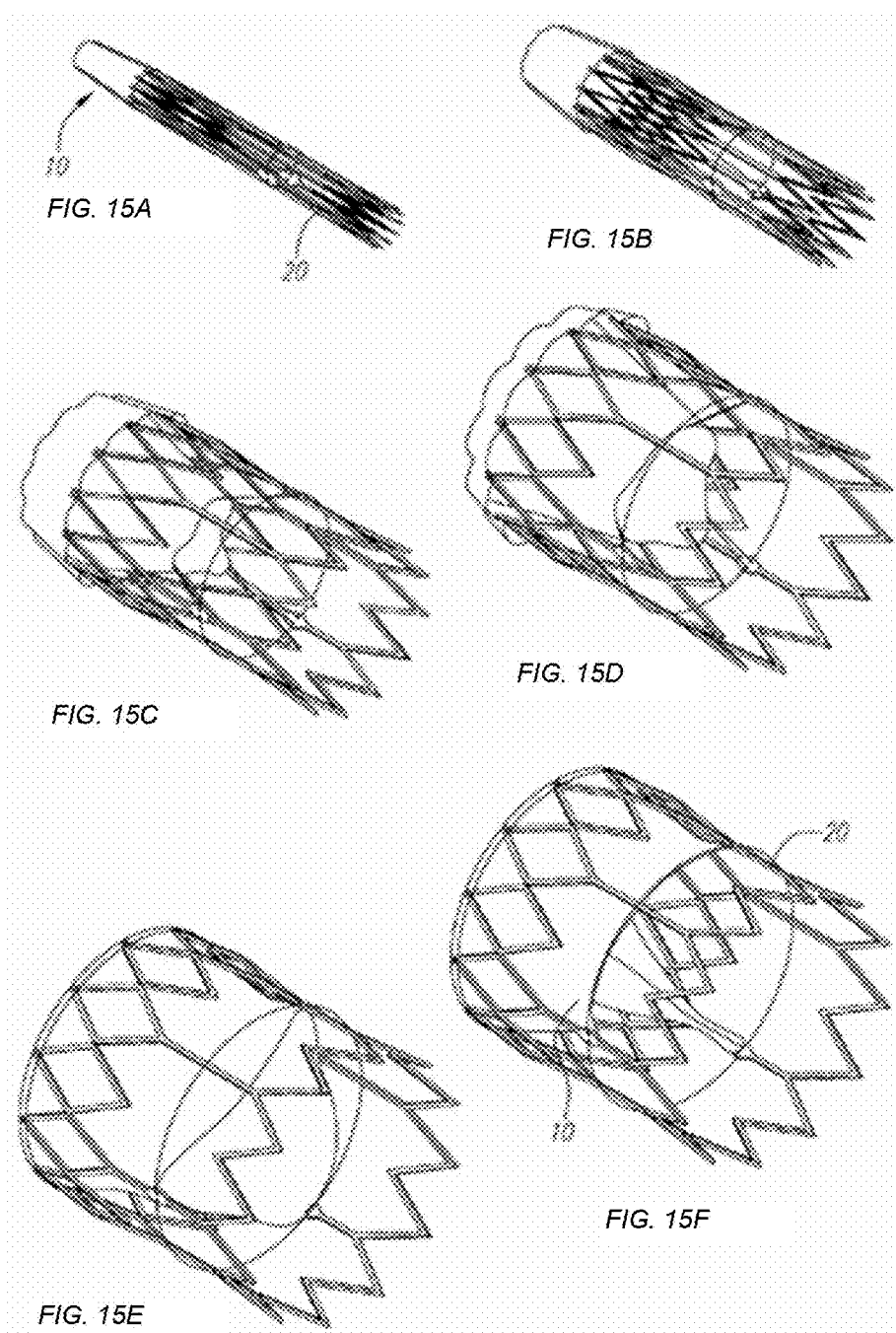
FIGS. 15A-15F are perspective views illustrating an example embodiment of a stent frame and valve in various stages of deployment as may be employed in connection with the embodiments herein.

A heart flow simulator was used for the experiments (FIG. 14, D). The components of the system are the Plexiglas container and silicon ventricular sac. The system is connected by a pulsatile pump system. The ventricular sac is suspended over the Plexiglas container, and the ventricular beating is generated as the ventricular sac's response to input waveform.

We used three types of aortic valves, i.e., control valve (FIG. 14, A), polymeric valve with moderate calcification on aorta-side leaflets (FIG. 14, B) and polymeric valve with severe calcification on both sides of leaflets (FIG. 14, C). Each aortic valve was placed in aortic valve position (FIG. 14, E-F).

VOLCANO s5™ imaging system with Visions PV 0.035 catheter (Volcano Corporation, Rancho Cordova, Calif.) was used. The IVUS catheter was advanced from the distal site of the aortic valve to the inside of ventricle across the aortic valve and manually pulled back with obtaining the IVUS imaging (FIG. 14, D). The IVUS imaging was obtained under both beating and non-beating condition.

To compare the echogenicity of artificial valve leaflets, the mean brightness level was calculated using image processing.

Results

For the control non-calcified valve, IVUS imaging showed the smooth surface of the leaflets (FIG. 14, G). The thickness of the leaflets were uniformly measured as 1.0 mm. For the polymeric valve with moderate calcification on aortic-side leaflet, rougher surface of leaflets as well as higher echogenicity was observed compared to the control valve. The thickness of the leaflet was measured as 1.5 mm (FIG. 14, H). For the severely-calcified polymeric valve, the leaflets' surface was roughest and generated the highest echogenicity among the three studied valve models. The thickness of the leaflets was measured as 1.8 mm (FIG. 14, I).

Quantitative evaluation of the valve leaflets echogenicity showed that the brightness levels of the control valve, polymeric valve with moderate calcification on aortic-side leaflets and polymeric valve with sever calcification on both side of the leaflets were 38.9, 53.5 and 79.3, respectively. These result were consistent with the qualitative assessment.

Conclusion

IVUS is a suitable imaging modality for characterization of valvular calcification and can be integrated within the delivery system of the transcatheter aortic valves for improved positioning and to minimize the chance of valvular calcific emboli and dislodgement.

Example 2

Percutaneous Heart Valve Delivery Systems

Embodiments described herein address the need for improved catheter devices for delivery, repositioning and/or percutaneous retrieval of the percutaneously implanted heart valves. One embodiment employs a plurality of spring-loaded arms releasably engaged with a stent frame for controlling expansion for valve deployment. Another embodiment employs a plurality of filaments passing through a distal end of a pusher sleeve and apertures in a self-expandable stent frame to control its state of deployment. With additional features, lateral positioning of the stent frame may also be controlled. Yet another embodiment includes plurality of outwardly biased arms held to complimentary stent frame features by overlying sheath segments. Still another embodiment integrates a visualization system in the subject delivery system. Variations on hardware and methods associated with the use of these embodiments are contemplated in addition to those shown and described.

Transcatheter aortic valve replacement (TAVR) procedures require image-guidance during implantation to successfully deploy the heart valve into the correct position within the patient's aortic annulus. Current image technology uses X-Ray, CT, MRI, or ultrasound to visualize the surrounding anatomy. However, only X-Ray can be used during the procedure for image guidance. X-Ray is not sufficient for visualization because it is a 2D projection of 3D anatomy that depends on the orientation angle of visualization. Currently, other imaging modalities can be used prior to the procedure and during follow-up, with the hopes that anatomical visualization can be directly correlated to the X-Ray images seen during the procedure. However, differences in contrast, resolution, and artifacts can produce differing results.

Correct valve positioning is crucial for treatment success and optimal outcomes after transcatheter valve implantation. For example, to maintain a stable and correct lengthwise position with respect to the aortic annulus, a stepwise deployment that allows the valve to be repositioned both circumferentially and in the axial direction (i.e., towards the left ventricle (LV) or the ascending aorta) is important.

However, most of the current technologies are limited by instant deployment, and once the valve is deployed, repositioning and/or percutaneous retrieval is not possible—or at least difficult or potentially problematic. Placement of the stented valve in a position that is too high (or proximal) can totally or partially obstruct the coronary ostia in a case of aortic implantation, which may result in myocardial infarction or ischemia. Additionally, if the valve is placed too high in the aorta, it may embolize into the aorta causing significant paravalvular regurgitation. On the other hand, implantation in a position that is too low (or distal) is accompanied by compression of the atrioventricular (AV) node in the membranous septum, which leads to conduction abnormalities.

Further technical developments with a focus on a positionable, repositionable, and/or percutaneously retrievable valve design allow optimal placement and may thereby significantly reduce the risk of paravalvular aortic regurgitation, myocardial infarction, or ischemia related to improper positioning. Likewise, advances in imaging to facilitate optimal heart valve placement are needed.

The embodiments described herein address the need for improved catheter devices for coordinated delivery, positioning, repositioning and/or percutaneous retrieval of the percutaneously implanted heart valves. The delivery system apparatus is a tool that may incorporate a guide wire lumen. As such, a given device may be suitable for so-called "over-the-wire" use and include a delivery sheath covering that restrains the stent frame of the valve. Alternatively, the delivery device may be tracked trough a catheter serving such function, as in a so-called "guide" or "delivery" catheter.

In one embodiment, the delivery apparatus includes a number of arms (such as, but not limited to three) embedded within its body that hold the valve's stent during the delivery procedure when it is in the collapsed state. The arms are equipped with adjustable springs that are remotely controllable by the operator, and allow for robust radial expansion or deployment of the collapsed stent in increments.

In use, the arms remain attached to the valve stent frame until the stent frame is fully deployed. If the stent/stent frame is not properly deployed, the arms, which are still releasably attached to the stent until intended release, can be used for partial contraction of the stent for repositioning purposes. When the stented valve is properly positioned as desired within the heart, the arms will be released from the stent, and return to their embedded/retracted positions within the apparatus. Then the entire apparatus is retracted. It may be retracted from the heart or vasculature over any guide wire used and/or through any delivery catheter employed for site access.

In another system embodiment allowing for stented valve delivery, repositioning, and/or percutaneous retrieval, draw line filaments are positioned through the distal end of a pusher sleeve (or draw tube), along a lumen of the sleeve (or tube), out through holes in the sleeve (or tube), out through proximal frame holes, along the surface of a heart valve frame, in through distal frame holes, in through the distal end of the sleeve (or tube), along the lumen of the sleeve (or tube), and out the proximal end of the sleeve (or tube). Variations on this approach are possible as are various optional features of the stent frame facilitating such use.

The draw lines may comprise polyester (PE), PTFE, suture material, or another high strength (and preferably biocompatible fiber) braid or bundle of fibers such as ultra-high-molecular-weight polyethylene (UHMWPE, sometimes shortened to UHMW). In this embodiment and others described herein, the heart valve frame may comprise superelastic NiTi alloy heatset in a desired shape, it may be constructed of a so-called "engineering plastic" such as polyetheretherketone (PEEK) or may be constructed otherwise. Various surface treatments or finishes may be desirable. In the case of a NiTi (Nitinol) or another metallic material implant, an electro-polished surface may be preferred.

Collapsed and expanded states of a heart valve can be controlled by varying the position and/or tension applied to the draw lines. A customized handle may be provided for user interface. Draw line tension can be increased until the heart valve frame is fully collapsed and fully releasing the draw line tension allows the self-expanding heart valve frame to fully expand. The heart valve frame may be put in an intermediate state by varying the tension applied to the draw lines. Moreover, the system can be setup to allow a range of lateral control of the stent position during delivery. In one variation, a "joystick" control interface is provided; in another a model of the implant (or at least the stent frame portion of the valve to be delivered) is used.

In yet another delivery system embodiment allowing for delivery, repositioning, and/or percutaneous retrieval, different means or entities are provided to control the state of device deployment (variably, from fully collapsed to fully expanded) of the proximal end of a self-expanding heart valve device. Such means or entities pertain to the use of multiple sleeve or sheath features (herein optimally referred to as "zip tube" parts or an assembly with "zip tube" sheaths or fingers) provided to mechanically change an angle between adjacent strut elements and thereby the proximity of the struts. In use, the zip tube sheaths (or fingers) collapse the heart valve frame by "zipping" the struts into closer proximity.

In this embodiment, the ends of a self-expanding heart valve frame are configured with a link feature. A self-expanding retainer is constructed and configured with diametrically collapsible retainer arms or fingers. A zip tube part or assembly with diametrically expandable/collapsible sheath fingers is configured in such a manner to allow the zip tube fingers to slide over the retainer fingers. The ends of the retainer fingers are configured with a clasp or link feature so as to mate to the heart valve frame clasp or link features.

The zip tube assembly may be partially advanced (distally) to trap the heart valve frame and retainer such that they will not unlink because the inner diameter (or inner dimension(s)) of the zip tube fingers are constructed so as to constrain the linked heart valve frame and retainer from unlinking when positioned around the linked frame or retainer. With the retainer serving as a means to secure the valve in position, the zip tube assembly may be variably advanced (relative to the linked heart valve frame or retainer) to variably (e.g., partially) collapse the proximal end of the heart valve device or fully advanced to fully collapse the proximal end of the heart valve device.

The zip tube part assembly may be variably retracted to allow the proximal end of the self-expanding heart valve device to variably (partially) expand or retracted sufficient to allow the self-expanding heart valve device to fully expand. Alternatively, the zip part or assembly may be secured in position and the retainer may be variably retracted to variably collapse the proximal end of the heart valve device up to fully collapsed or variably advanced to allow the self-expanding heart valve device to variably expand up to fully expanded. The zip tube part or assembly can be fully retracted allowing the heart valve frame and retainer to unlink thereby releasing the heart valve device from the delivery system so that the heart valve device may be left in position and the delivery system may be removed.

In addition, any of the subject delivery system architectures may incorporate a visualization system for image-directed heart valve delivery. Alternatively, other features for restraining and/or manipulating a self-expanding stent frame or a ballooned stent frame approach may be employed in an image-guided system. All of these embodiments involve a catheter or catheter-like device that utilizes an integrated imaging modality with a deployment mechanism. As such, these embodiments may be used to accurately deploy a heart valve into a patient with greater accuracy and precision than with current procedural imaging modalities where direct visual confirmation is not possible.

In these embodiments, the delivery system incorporates a catheter-based imaging modality within the device, such as, but not limited to, intravascular ultrasound (IVUS), intravascular photoacoustic (IVPA) imaging, optical coherence tomography (OCT), raman spectroscopy, or an optical method, capable of detecting features of a vessel in which the catheter is inserted. The selected imaging systems allow clinicians to image both the surrounding anatomy and the advancing catheter in real-time during the procedure.

In one example, since IVUS is a tomographic imaging modality, a 3D image of the aortic root can be produced through pull-back imaging. High-resolution IVUS is well-known for interrogating the lumen wall of vessels and has also been used to visualize metal stents in vivo. In the example of IVUS hardware, a physician can accurately image and position the implantable valve device without the use of ionizing radiation or nephrotoxic contrast agents. Furthermore, IVUS advantageously provides for a real-time imaging modality.

A catheter system can be based upon an imaging catheter or a valve delivery catheter. In an embodiment where the catheter system is based upon the valve delivery catheter, the imaging modality device can be inserted through the center of the valve delivery catheter, where the active imaging element is aligned with a feature of the valve delivery catheter, such as, but not limited to the catheter tip, the distal or proximal end of the valve stent, or some other predetermined landmark of the valve delivery catheter. Positioning of the imaging device on the circumference of the valve delivery catheter is also possible in another embodiment to prevent visual hindrance from the implanted stent.

In yet another embodiment, the valve delivery system is based upon the imaging catheter, and the deployment mechanism is inserted through the lumen of the imaging catheter, such as, but not limited to, through a guidewire port of the imaging catheter. Furthermore, the delivery system referred herein is not limited to the delivery of a heart valve device, but could be used to deliver therapy to a localized region through the use of a catheter. Such examples of delivery could include, but are not limited to, delivery of drugs or other therapeutic agents, delivery of RF irradiation, or delivery of another device.

Operation of the delivery system allows visualization of the surrounding anatomy during insertion of the imaging catheter in the context of the location of the delivery catheter. As such, the location of the delivery catheter relative to the surrounding environment may always be known. In one embodiment, the delivery system is fixed relative to the imaging transducer within the catheter. In another embodiment, the two components can be moved relative to one another. However, in embodiments where relative motion is allowed, the relative motion is advantageously tracked or known in order to maintain accuracy in the advancing catheter.

The subject delivery devices, kits in which they are included (with and without valve installation or assembly), methods of use and manufacture (such as assembly of the delivery system and frame alone and/or with included valve) are all included within the scope of the present disclosure. Some aspects of the same are described above; more detailed discussion is presented in connection with the figures below.

Other systems, devices, methods, features, and/or advantages of the subject matter described herein will be or will become apparent to one with skill in the art upon examination of the following figures and detailed description. It is intended that all such additional systems, devices, methods, features, and/or advantages be included within this description and be within the scope of the subject matter described herein, regardless of whether recited in this summary section. In no way should the features of the example embodiments in this or any other section be construed as limiting the appended claims, absent express recitation of those features in the claims.

Various example embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act, or step to the objective(s), spirit, or scope of the present inventive subject matter. All such modifications are intended to be within the scope of the claims made herein.

FIGS. 15A-15F illustrate an implant 2 and a suitable approach to valve 10 attachment and its manipulation for delivery in coordinated use with an expandable stent frame 20. Further details as to valve construction and/or its manipulation for delivery may be appreciated in review of U.S. Pat. No. 8,133,270 to Kheradvar, et al., incorporated by reference herein in its entirety for all purposes. Features of the stent frame elaborated upon below in the various embodiments may be added to those shown in FIGS. 15A-15F or used in connection with other suitable stent frame and/or other valve architectures.

In any case, implant 2 (e.g., valve 10 and stent frame 20) is directly applicable for coordinated use with a delivery system as shown in FIGS. 16A-16B. More specifically, a delivery system apparatus for controlled deployment of a stented heart valve system in increments is shown. The system provides for repositioning a stented heart valve system during and after deployment. As variously illustrated, device 100 includes a plurality of deployable arms 110. These are adjustably deployable. The arms are first embedded inside the apparatus. FIG. 16B illustrates the location of one of the embedded arms 110 within a delivery device sleeve 120. For tracking to the target site, the arms are hidden. The arms exit the sleeve through ports or slots 122 in the wall of the sleeve. The arm lengths are adjustable and the arms are releasably attached to the stent of the stented valve. As shown in FIG. 16B, each arm may be equipped with an in-line adjustable spring that is controllable by the operator remotely. As illustrated in FIG. 17, such actuation allows for robust radial expansion or deployment of the collapsed stent frame in increments.

The arms remain attached to the stent until the stent is fully deployed. During tracking to a site for deployment, the stented valve may be covered by a sheath incorporated in the delivery system or pass within a delivery catheter (either case illustrated by an optional sleeve 140). If the stent is not properly deployed, the arms, which are still releasably attached to the stent, can be used for partial contraction of the stent for repositioning purposes. When the stented valve is properly positioned within the heart, the arms will be released from the stent, and return to their embedded positions within the apparatus. Then the apparatus will be retracted into the sheath or through the delivery catheter from the heart or vasculature.

As seen in FIG. 18A in which the stent frame is detached, each arm may terminate in a releasable hook, jaw, clevis 112 or the like for such purpose(s). The connection and release may be provided by a simple snap fit. Otherwise it may be provided by a more active means for stent frame interface as illustrated in FIG. 18B, that shows an arm comprising a hollow micro tube or sheath 114 with spring loaded strings or filaments 116 inside where a string or filament 118 inside the guide tube or sleeve 120 can be used to control the closing and opening of the hooks 112.

FIGS. 19A-19E illustrate progressive stages of implant deployment and recapture for a second embodiment. Here, in a system pictured for over-the-wire tracking to its deployment site, a delivery system 200 includes a sheath 210 (with distal radiopaque marker 212) coaxial with a pusher sleeve 220. A distal portion of sleeve 220 includes apertures 222 through which filaments 230 pass into and proximally within the length of the sleeve. The filaments loop from these apertures through proximal stent frame apertures 22 and more distal stent frame apertures 24 (or alternatively past strut junctions in a different stent configuration) and into a distal end 224 of the sleeve (or a second set of distal apertures (not shown) in the sleeve if so-desired). Such details of the sleeve are shown unobscured in FIGS. 20A-20C, as is an optional shoulder 226 for abutting proximal end or crown sections 26 of the stent frame and guide sheath 210 of the proximal end or crowns of the stent frame.

Figure 21A:
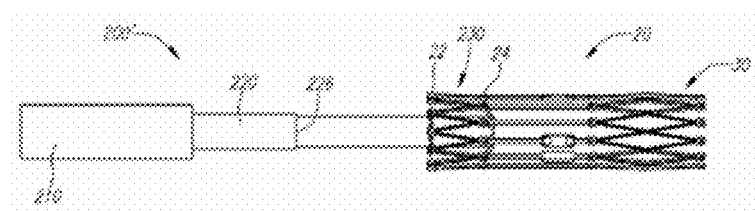
FIGS. 21A and 21B are side views illustrating the sent frame associated with the delivery device sleeve in contracted and expanded states, respectively.
Figure 21B:
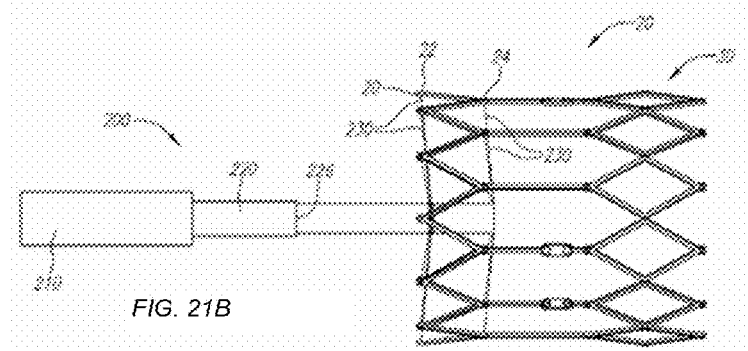

Regarding interaction between the stent frame and delivery system 200, FIGS. 21A and 21B provide side views of the stent frame associated with the delivery device sleeve in contracted and expanded states, respectively. Here, the manner of stent frame expansion and contraction as related to extended filament 230 length is clearly visible.

FIGS. 22A and 22B further illustrate such details as described above. When assembled in a delivery system 200, stent frame 20 will be captured within loops 232. The assembled relation of elements is shown in each of FIGS. 23A-23C and FIGS. 24A and 24B. Comparing FIGS. 23A-23C to FIGS. 24A and 24B, the state of the stent frame is changed from open or expanded in the former trio of figures, to compressed in the latter pair.

Such control is achievable by remote actuation of the loop filaments with a customized handle or other user interface means. Any handle may include means for group control of the filaments and independent control of sheath position. Such a handle 240 may include separate "grip" 242 and "plunger" or "slide" 244 interfaces as illustrated by example in FIG. 23A for such purposes. Otherwise, mechanism internal to the handle can automate all of the various control procedure(s) by actuating a grip 242, alone.

FIGS. 23A and 23B also offer good illustration of the manner in which filaments 230 pass through apertures 22, 24 and run along interposed strut sections 28. FIG. 23C illustrates the radial relationship of the apertures and filament 230 portions. Here, a crossing segment 234 of the filament between the apertures 22 and 24 is positioned outside of and opposing strut section 28. The crossing segments are angled with the struts when the stent frame is in an expanded state and more close to axially aligned when the stent is compressed as shown in FIGS. 24A and 24B.

As noted above, the transition between the open and compressed states (and states therebetween) is managed by letting-out or reeling-in the draw line filament determining the size of the control loop. Ultimately, one end of the line is pulled all of the way through the stent aperture to finally release the implant.

FIGS. 19A-19E illustrate a range of activity that is possible in terms of device manipulation before such release. In succession, these views show progressive stent frame deployment and steps toward complete recapture.

Figures 19A, 19B, 19C, 19D, 19E:
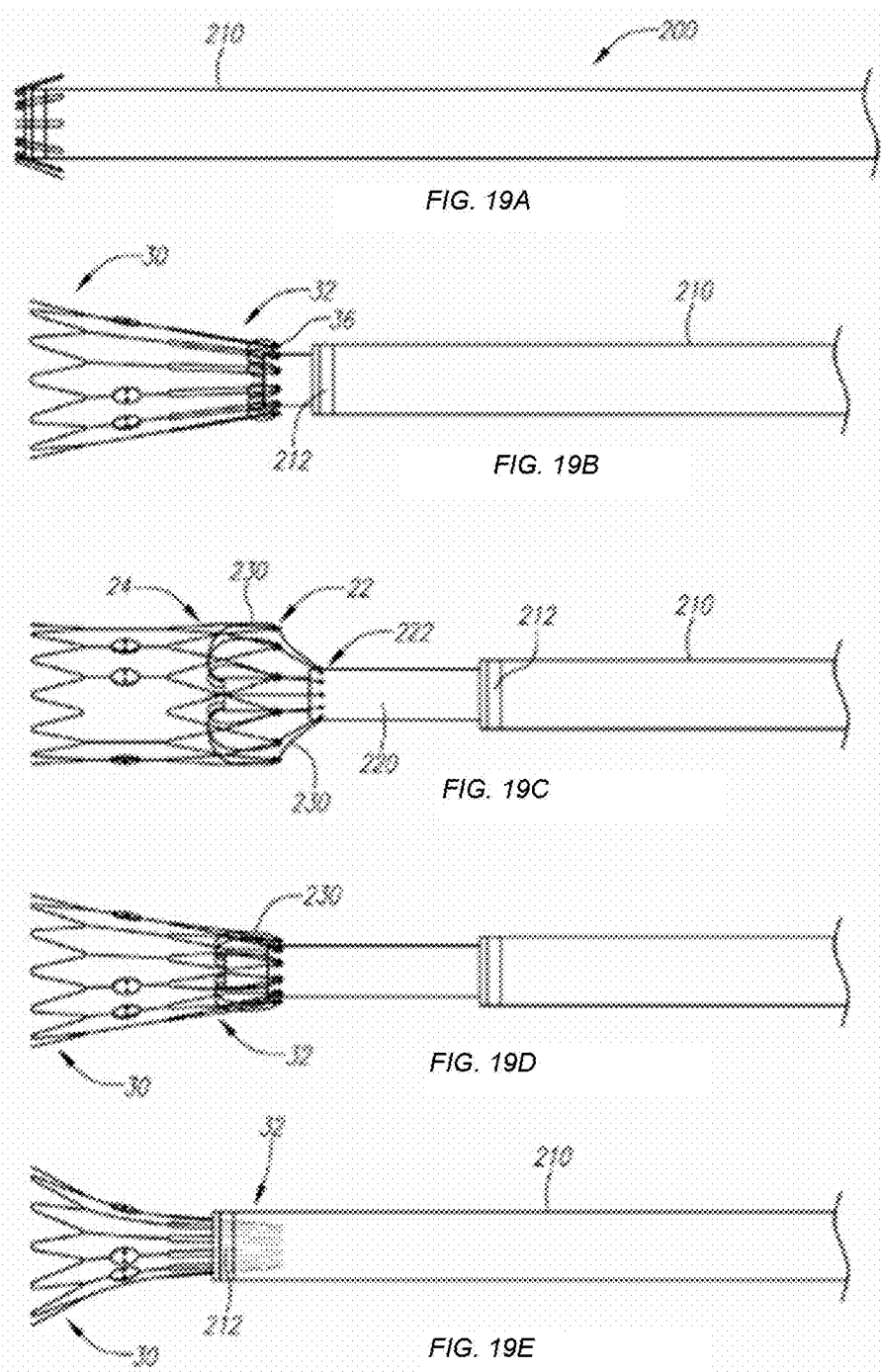
FIGS. 19A-19E illustrate progressive stages of stent frame deployment and recapture for a second embodiment.

FIG. 19A pictures (literally, given that the figures are based on photographs) the beginning of stent frame deployment as sheath 210 is withdrawn and a distal end 30 of the stent self-expands. FIG. 19B shows the sheath fully withdrawn and full tension on the draw lines or filaments, maintaining a proximal side 32 of the stent 20 in a compressed state. As in FIG. 19D illustrating the same (but in the case of FIG. 19D re-compression after the relaxation of draw lines to allow expansion as in FIG. 19C), the sheath can be advanced to fully recapture the stent frame. With the beginning of such action shown in FIG. 19E, the stent frame can be fully recovered within sheath 210—whether for the purpose of repositioning or bulk retrieval of the device.

Figure 25A:
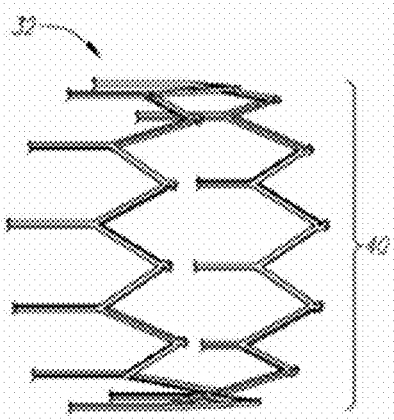
FIGS. 25A and 25B are partial perspective and detail side views, respectively, illustrating a stent frame for a third embodiment.
Figure 25B:
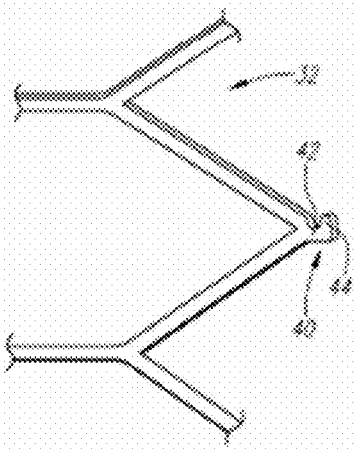
Figure 26:
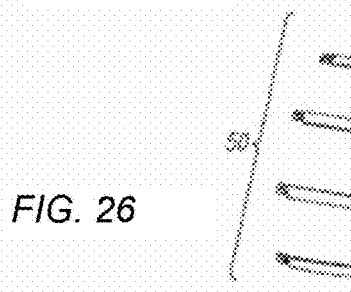
FIG. 26 is a perspective view illustrating a frame retainer with retainer fingers.

A third delivery device embodiment is able to offer similar advantages in terms of delivery, repositioning, and/or percutaneous retrieval. Stent frame components of such a system are shown in FIGS. 25A and 25B. In each view, a proximal end 32 of a stent frame 20 includes clasp features 40. Each clasp feature 40 may comprise a bridge section 42 and an overhang section 44. Complementary clasp features 50 are provided at the end of resilient retainer "arms" or "fingers" 52 associated with a delivery system pusher. Arms 52 may comprise Nitinol or another elastic or superelastic material. Arms 52 are biased outward such that they spring out to a position as shown in FIG. 26 when released from restraint (e.g., upon exiting a delivery system sheath element or delivery/guide catheter body). Arms 52 are joined or meet at a hub 54. These components may be cut from a single hypotube or polymer sleeve that extends to the proximal end of the delivery system (not shown) as one piece or be assembled using conventional techniques such as laser welding, etc. In any case, pairs of complementary clasp elements 40/50 are releasably engaged in sheaths 60.

Figure 27A:
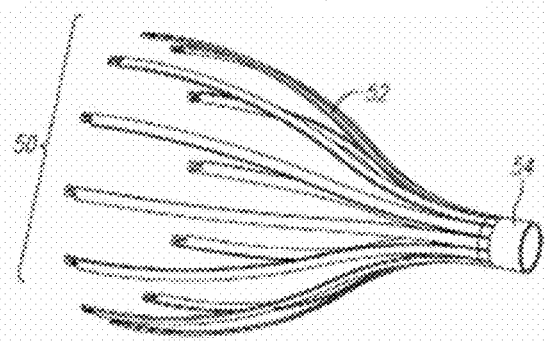
FIGS. 27A and 27B are perspective and end views, respectively, illustrating a zip tube part or assembly and zip tube fingers.
Figure 27B:
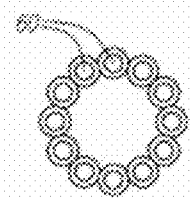

FIGS. 27A and 27B illustrate a construct in which multiple sheaths 60 extend to and join at a hub 62 optionally extending proximally as a single sleeve 64. Such a structure can be produced by bundling and reconfiguring (e.g., by fusing) a plurality of thermoplastic sheaths, bundling and bonding a plurality of sheaths, and splitting an end of a multi-lumen extrusion into a plurality of separate sheaths. Other means of construction will be appreciated by those of skill in the art as well.

Figure 28A:
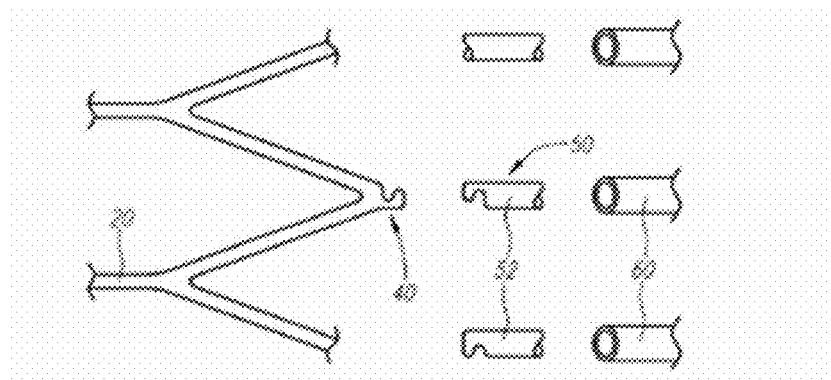
FIG. 28A illustrates segments of an expanded heart valve frame, retainer fingers, and zip tube fingers as associated in the subject embodiment.
Figure 28B:
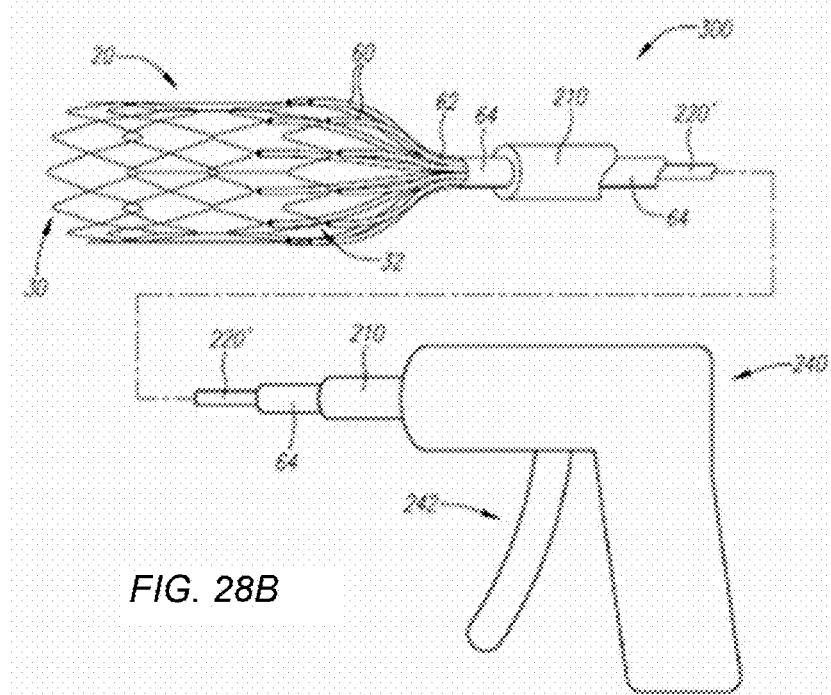
FIG. 28B illustrates a complete assembly of the embodiment including these subcomponents.

Regardless, FIG. 28A provides a partial assembly drawing illustrating the axial alignment for a plurality of interfacing members. FIG. 28B shows the same components of the third device embodiment brought together in a completed apparatus assembly 300. As in the embodiments above, such a system may optionally include a cover sheath 210 and a handle 240. In addition, system 300 may include an innermost elongate sleeve 220' optionally providing a lubricious PTFE liner for a guidewire lumen and/or column or "push" strength to the system.

Figure 29A:
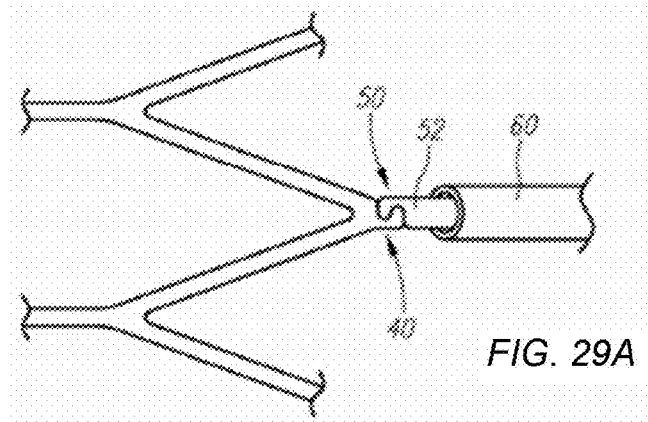
FIGS. 29A-29F are detail side views illustrating operation of elements within the embodiment.
Figure 29B:
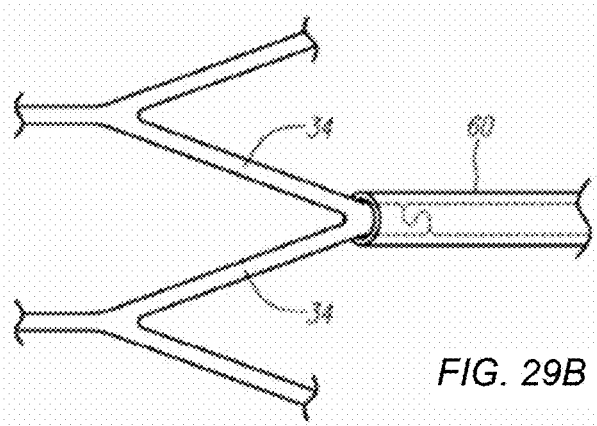
Figure 29C:
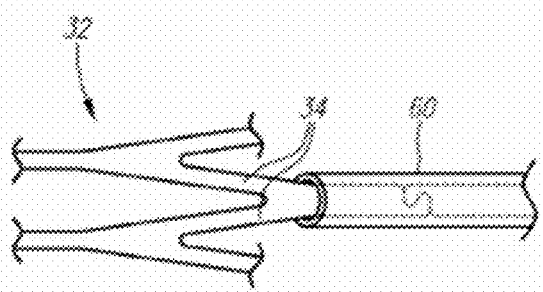
Figure 29D:
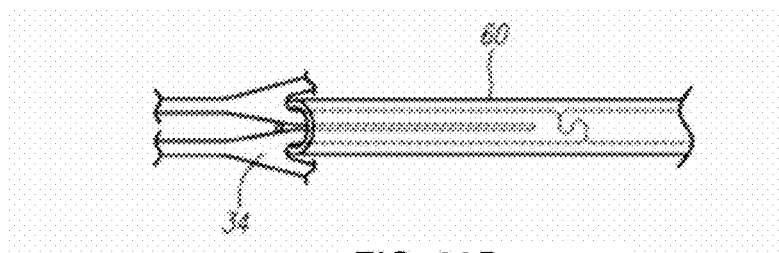
Figure 29E:
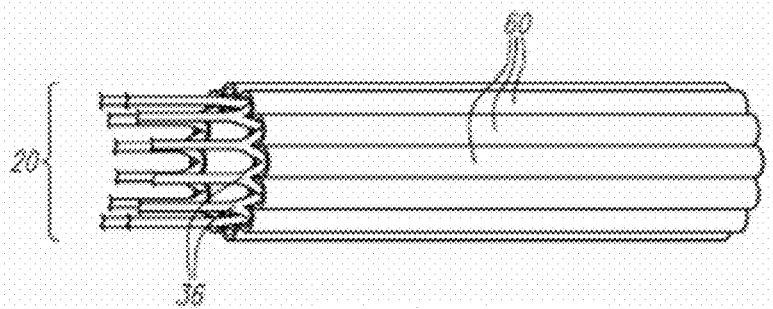

FIGS. 29A-29F illustrate the operation of an intended interaction of the subcomponents of system 300. In FIG. 29A, the heart valve frame clasp or link 40 is interfaced with clasp/line 50. In FIG. 29B, clasps features 40/50 are trapped within sheath 60. At this point, further withdrawal of stent frame 20 into sheath element 60 or (stated otherwise) advancement of sheath 60 over adjacent proximal stent struts 34 results in a condition as shown in FIG. 29C. Here, struts 34 are brought together collapsing the entirety of the proximal end 32 of stent frame 20 (given that the same condition is achieved around the entire periphery of the stent by paired device features). As shown in FIG. 29D, sheath 60 can cover the entirety of struts 34 up to their junctions 36 with adjacent struts. The net effect is shown in FIG. 29E where the entire proximal side of the stent frame 20 is compressed efficiently by the multiple sheath elements shown.

As summarized above, the zip tub part assembly (sheaths 60 and associated components) may be variably retracted to allow the proximal end 32 of the stent frame to partially expand or retracted sufficiently to allow the stent frame to fully expand. Alternatively, the zip part/assembly may be secured in position and the arm retainer 54 retracted to variably collapse the proximal end of the heart valve device (up to fully collapsed) or variably advanced to allow the self-expanding heart valve device to variably expand (up to fully expanded). Further action associated with collapse/compression and expansion of the stent frame is achieved by covering and uncovering the stent frame with optional sheath 210 or by a guide catheter.

Figure 29F:
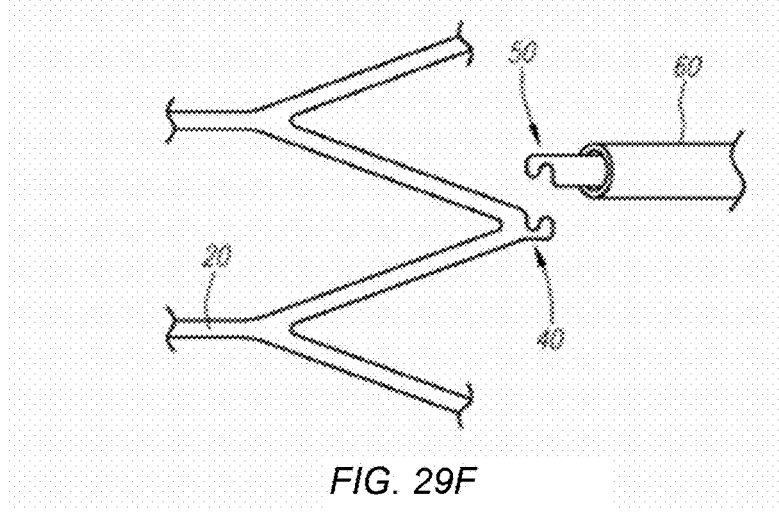

In any case, upon achieving desired implant placement, clasp elements 40/50 can be freed from confinement within the sheath member(s) 60 thereby unlinking the elements allowing stent frame 20 release as shown in FIG. 29F and allowing delivery system withdrawal from a patient in a successful percutaneous heart valve implantation procedure.

Figure 30A:
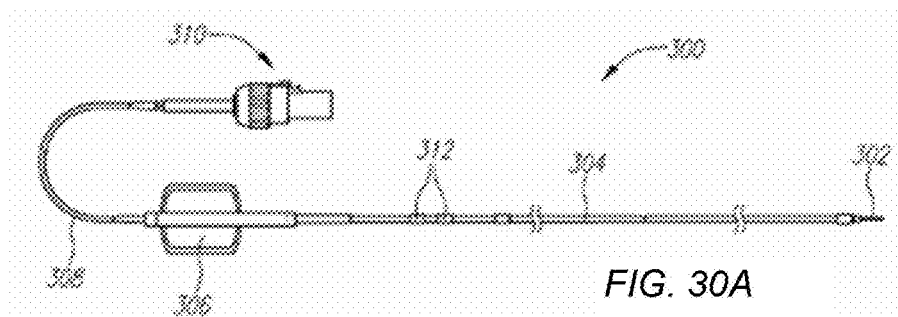
FIGS. 30A and 30B are side views illustrating an example embodiment of imaging catheter and stent frame components of an imaged-guided delivery system.
Figure 30B:
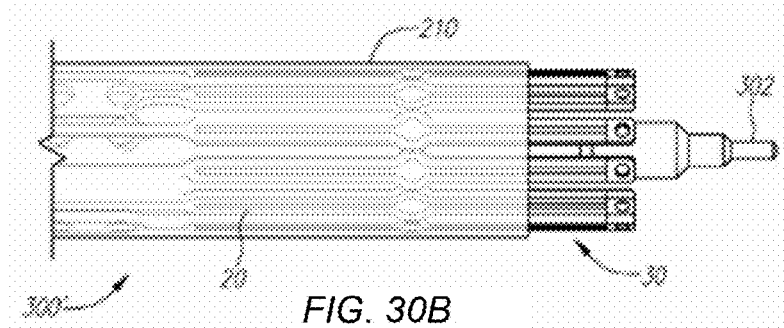

FIG. 30A illustrates a suitable IVUS catheter 300 for use in an image-guided valve delivery system according to another embodiment. The figure shows an EAGLE-EYE IVUS imaging catheter (Volcano Corp). Imaging catheter 300 includes a distal transducer tip 302, an intermediate catheter shaft or body 304, handle/grip 306, lead 308, and a proximal connector 310. Radiopaque shaft markers 312 are provided that may be relocated or additional markers added for coordination with a valve delivery catheter to (together) provide an overall valve delivery catheter system (e.g., by inserting catheter 300 within delivery system 100 or 200 as previously illustrated).

A distal portion of such a combined system 300' in shown in FIG. 30B. This photograph shows a distal end 30 of a TAVR stent 20 compressed to 4.3 mm diameter (13 Fr). It is held in a sheath 210 that may form part of an overall delivery system 300'. Otherwise, it may be regarded as a loading sheath or surrogate (or stand-in) for a delivery catheter through which the stent 20 will track in a medical procedure. As shown, an ATLANTIS SR PRO IVUS transducer (Boston Scientific Corp.) 302 is placed through the center of the valve stent frame 20 for sizing purposes.

The image does not show the valve leaflets (e.g., as in FIGS. 15A-15F) for the overall implant that contribute to the inner diameter space constraints or the specific delivery system features that may be employed. Yet, the image illustrates the general hardware (stent frame, delivery system/sheath components and IVUS device) that may be employed in the subject systems and methods.

Figure 31:
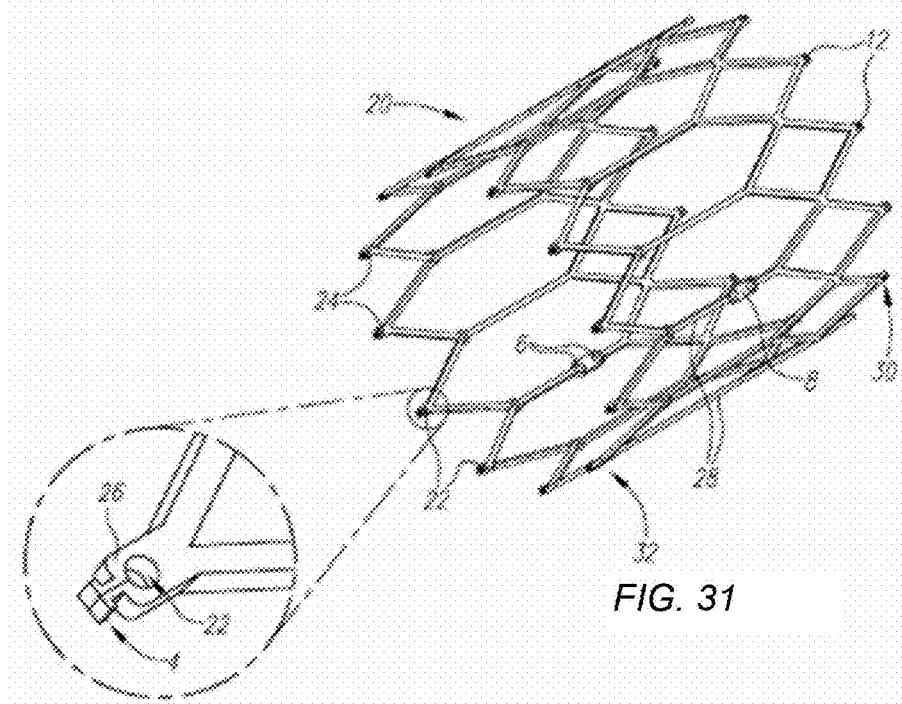
FIG. 31 is an enlarged perspective view of a stent frame component as previously illustrated.

FIG. 31 is a perspective view of a stent frame 20 component that may be employed therein. Actually, this figure provides an enlarged view of the stent frame shown in FIGS. 21A and 21B. So-enlarged, features in addition to those of the stent in U.S. Pat. No. 8,133,270 upon which the overall architecture may be based are easily highlighted. Specifically, two sets of holes 22 and 24 (proximal and more distal) are provided at the proximal side 32 of the stent frame 20 (i.e., on the "top" of the stent that would be positioned in the aortic root). These holes allow for passage of a network of pull-strings or filaments used for step-wise deployment, repositioning of the stent, and retrievability back to the guidewire catheter (as discussed above) and also lateral positioning (as discussed below). Further, T-shaped structures 4 at the proximal side 32 are added to proximal crown features 26 to accommodate repositioning and retrievability of the valve during implantation procedure by way of attachment to complimentary delivery system features 40 like the example shown in FIGS. 28A and 28B.

In addition, connector holes 6 in tabs 8 of material at the middle of a number of struts 28 are provided to accommodate locking with pin-shape structures that permanently affix/connect the valve 10 material to the stent frame structure as further described in U.S. patent application Ser. No. 13/773,389 filed Feb. 21, 2013, which application is incorporated by reference herein in its entirety. A set of distal holes 12 at distal end 30 or "bottom" ventricular side of the stent advantageously provide attachment points (e.g., by suturing) of the valve leaflets to the stent frame as illustrated in FIGS. 15A-15F.

Figure 32A:
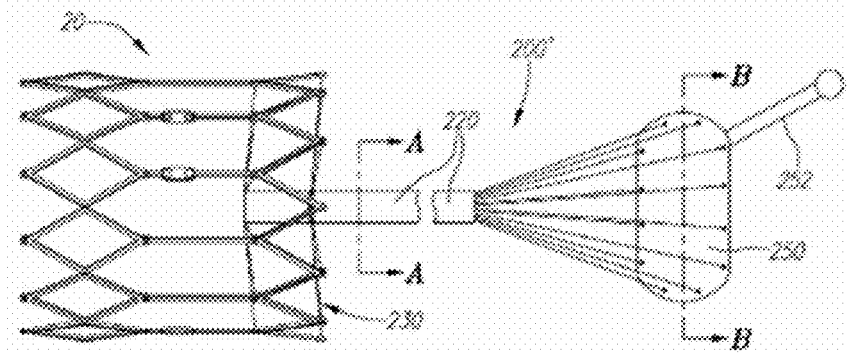
FIGS. 32A and 32B are side views illustrating the stent frame embodiment of FIG. 31 associated with a delivery device, with the stent frame in a neutral and a laterally displaced position, respectively.
Figure 32B:
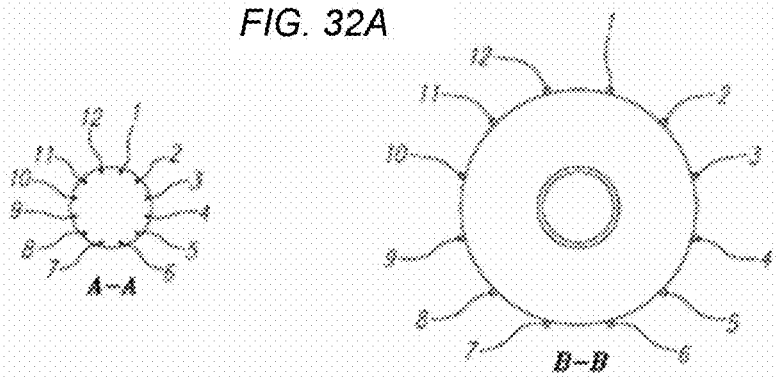

FIGS. 32A and 32B are side views of the same stent frame 20 associated with a delivery system 200' related to that in FIGS. 19A-24B, but including additional manipulation features. Specifically, delivery system 200' is adapted for controlling the lateral position of a heart valve device, for positioning or repositioning during deployment. Draw lines (or filaments) 230 (configured as in the referenced embodiments) are further connected to a pivot fitment 250 and a joystick-type handle 252.

As shown in FIGS. 33A and 33B loops or end ties 236 around spurs 256 may provide such a connection. As likewise shown, fitment 250 (alternatively, a boss, cap or housing) may ride upon or otherwise incorporate one or more spherical bearing surfaces 254/254'.

However configured, operation of system 200' is such that the angular ordering of the draw lines 230 in the overall heart valve (stent frame 20 shown) will correspond to the angular ordering of the draw lines on pivot fitment 250. Such activity is assured by the corresponding relationship of draw lines (or filaments) as shown in cross-sections A-A and B-B in FIG. 32A. The radial orientation of filaments 230 at the stent frame 20 and leading to the stent frame are matched with the radial orientation of the filaments at fitment 250 is indicated by the matching numeral position in the two cross-sectional views.

Therefore, as shown in FIG. 32B, tilting the pivot fitment 250 (e.g., by leaver arm/joystick 252) causes coordinated pull and release (or relaxation) of the draw lines proportional to the angular ordering and the direction of tilt to drive a corresponding change in the lateral position of the heart valve device (denoted by the directional arrows). Thus, the lateral position of the heart valve device can be controlled and manipulated by tilting the pivot fitment. While a joystick or similar interface can be incorporated into or connected to the pivot fitment to facilitate control of the tilt mechanism, other approaches including remote/robotic control are contemplated as well.

In any case, FIGS. 33A and 33B are photographs of a functional prototype 200" of the delivery system embodiment diagrammatically shown in FIGS. 32A and 32B. Here, blocks 260, 262 simulate the end constraint conditions of a catheter body. Between these, filaments 230 are visible (whereas they would generally be housed within a catheter body/sleeve). A short sleeve 264 extends from block 262 to simulate the distal portion of the catheter body 220 shown in FIGS. 19A-24B, 32A and 32B including its side apertures 222 and an end hole 224.

In FIG. 33A, stent frame 20 and pivot fitment 250 are shown in a neutral or "home" position. While being tilted/turned, as shown in FIG. 33B, pivot fitment 250 reorients the filaments 230 to move stent 20 laterally in relation to sleeve 264.

Finally, FIG. 34 diagrammatically illustrates an alternative user interface for the FIGS. 32A and 32B delivery system. Here, instead of using a handle, a model 260 of the implant 2 (or at least the stent frame 20) to be delivered is employed. The model may be a scale replica of the stent frame 20 and/or the entire implant 2. Generally, it will be configured in an expanded shape. However, it may be controlled so that its state of expansion matches that of implant 2. Alternatively, manipulation of the model expansion may alter the expansion state of the implant. Given all of these options, however, the model will generally at least serve as an interface for lateral valve positioning.

In which case, the model may be connected to the filaments in the same manner/fashion as the stent frame 20 to be manipulated along a catheter centerline 270 by movement of the model in any combination of lateral directions indicated by the axis arrows shown. Alternatively, model 260 may overlay and be connected to fitment 252 to which the filaments are connected (e.g., at spurs 254).

Use of the model 260 in manipulating the stent frame 20 and being able to visualize the direct correspondence of movement between the implant (via fluoroscopy or other medical imaging) to the sight of the model in hand may be particularly beneficial to a physician in attempting ideal implant positioning and placement. In a method of use, the method may comprise at least partially deploying stent frame 20 by withdrawing a sheath 210 covering the stent frame and relaxing the filaments 230 passing through a catheter sleeve 220 and attached to the stent frame to expand the stent frame (e.g., as in such activity shown in FIGS. 19A-19C). Then, a proximal interface such as a joystick or model is manipulated to move the stent frame laterally relative to the catheter sleeve by selectively tightening and relaxing the filaments (e.g., as in such activity shown in FIG. 32B relative to a zero or neutral position of fitment 252). Naturally, the device can be returned to center and then recompressed and/or resheathed for repositioning as well.

In the various delivery system architectures, the catheter/pusher shaft or sleeve may comprise a simple extrusion (e.g., PTFE, FEP, PEEK, PI etc.) or may be constructed using conventional catheter construction techniques and include a liner, braid support and outer jacket (not shown). Likewise, the various tubular members may comprise extrusion (per above), metal hypotube, etc. Further, the stent frame may be constructed using conventional laser cutting and electropolishing techniques and/or be otherwise constructed. In embodiments intended for tracking through a guide/delivery catheter without an incorporated sheath, a loading sheath (optionally peel-away or splittable) may be provided over the implant. Other typical percutaneous access instruments (such as wires, etc.), valves, and other hardware may also be employed in connection with the subject matter described herein.

The subject methods may include each of the physician activities associated with implant positioning, re-positioning, retrieval and/or release. Regarding these methods, including methods of manufacture and use, these may be carried out in any order of events which is logically possible, as well as any recited order of events.

Furthermore, where a range of values is provided, it is understood that every intervening value, between the upper and lower limit of that range and any other stated or intervening value in the stated range is encompassed within the invention. Also, it is contemplated that any optional feature of the described variations may be set forth and claimed independently, or in combination with any one or more of the features described herein.

Reference to a singular item includes the possibility that there are a plurality of the same items present. More specifically, as used herein and in the appended claims, the singular forms "a," "an," "said," and "the" include plural referents unless specifically stated otherwise. In other words, use of the singular forms allow for "at least one" of the subject item in the description above as well as the claims below. It is further noted that the claims may exclude any optional element and may explicitly limit each element to a "single" instance or "only one" such instance of that element. As such, this paragraph is intended to serve as antecedent basis for the use of such exclusive terminology as "solely," "only," "a single" and the like in connection with the recitation of claim elements, or the use of a negative limitation.

Without the use of such exclusive terminology, the terms "comprising," "including," and "having" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the different embodiments or aspects described herein is not to be limited to the examples provided and/or the subject specification, but rather only by the scope of the issued claim language.

Example 3

Delivery System for Transcatheter Detachment of Stent from the Delivery Device

Described is an apparatus for transcatheter detachment of a stent from a delivery device. A braided suture with an opening is inserted through a restraining hole in a glide (the opening is secured on one side by a knot or a series of knots) and a release line is inserted through the braided suture opening. The braided suture is thus prevented from pulling through the restraining hole while the release line is through the opening. The braided suture is free to pass through the restraining hole after the release line is pulled out of the opening and thereafter pulled free of stent holes formed through a stent, thereby detaching the stent at a desired location.

This invention is related to the field of stents. During transcatheter implantation of stents (e.g., valve housings or other stent-related deliveries) optimal positioning and placement of the stent is crucial for treatment success and optimal outcome. Once the stent has been optimally positioned it is equally important that it remains optimally positioned as the stent is being detached from the delivery system without undue stress or motion during detachment. Typical stent delivery systems suffer in that they may inadvertently alter the position of the stent during detachment.

Thus, a continuing need exists for a stent delivery system for transcatheter delivery and implantation that minimizes stress and motion of the stent during detachment.

The present invention relates to percutaneously-delivered stents and, more particularly, to associated stent delivery systems for transcatheter delivery and detachment of a stent. The delivery system includes a glide having a plurality of restraining holes therethrough. A plurality of draw lines are also included. Each draw line has an opening formed therethrough and is adapted to pass through a stent hole in a stent and thereafter through a restraining hole in the glide. A release line is included that has a distal end and a proximal end. The distal end of the release line is adapted to pass through the openings of the draw lines and affix a stent with the glide, whereby upon implantation, a user can pull on the proximal end of the release line, which pulls the release line from the draw lines to allow the draw lines to be drawn from the stent, thereby detaching the stent at a desired location.

In another aspect, each of the draw lines is formed of a braided suture.

In yet another aspect, the glide is formed as a cylindrical barrel, such that the draw lines extend from a delivery device and through the glide and out of a distal end of the glide, with the draw lines passing through the stent and into the glide through the restraining holes in the glide.

In another aspect, each braided suture is formed of at least three braided strands and has a distal end, with one or more knots formed proximal the distal end.

In yet another aspect, each of the braided strands is formed of a plurality of filaments and the opening in each draw line is formed by piercing through and separating the filaments such that approximately half of the filament reside on each side of the opening.

In another aspect, the release line has a diameter and each of the restraining holes in the glide have a diameter, such that the diameter of the release line is greater than the diameter of the restraining holes in the glide.

In yet another aspect, the draw lines extend substantially parallel with the release line, with the draw lines thereafter extending through the glide.

Finally, as can be appreciated by one in the art, the present invention also comprises a method for forming and using the invention described herein. For example, the method comprises acts of pulling a release line, such that upon pulling the release line, the release line is pulled free of openings formed through a plurality of draw lines, thereby releasing the draw lines from a glide; and drawing on the draw lines to pull the draw lines from restraining holes in the glide and stent holes in the stent, thereby detaching the stent at a desired location.

The disclosure relates to percutaneously-delivered stents and, more particularly, to associated stent delivery systems for transcatheter delivery and implantation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

Described is a stent delivery system for transcatheter delivery and implantation. The stent delivery system provides an improved system for stent detachment from the delivery device, such as but not limited to a delivery system of a transcatheter heart valve or any other stent. This invention addresses the need for improved detachment of the stent from the delivery system to minimize interactional forces between the delivery device and the stent during detachment (to minimize inadvertent movement of the stent during detachment). In doing so, the detachment points, in one aspect, are located on the stent (so that detachment is of relatively short duration), and are released nearly simultaneously (to minimize inadvertent movement).

Figure 35:
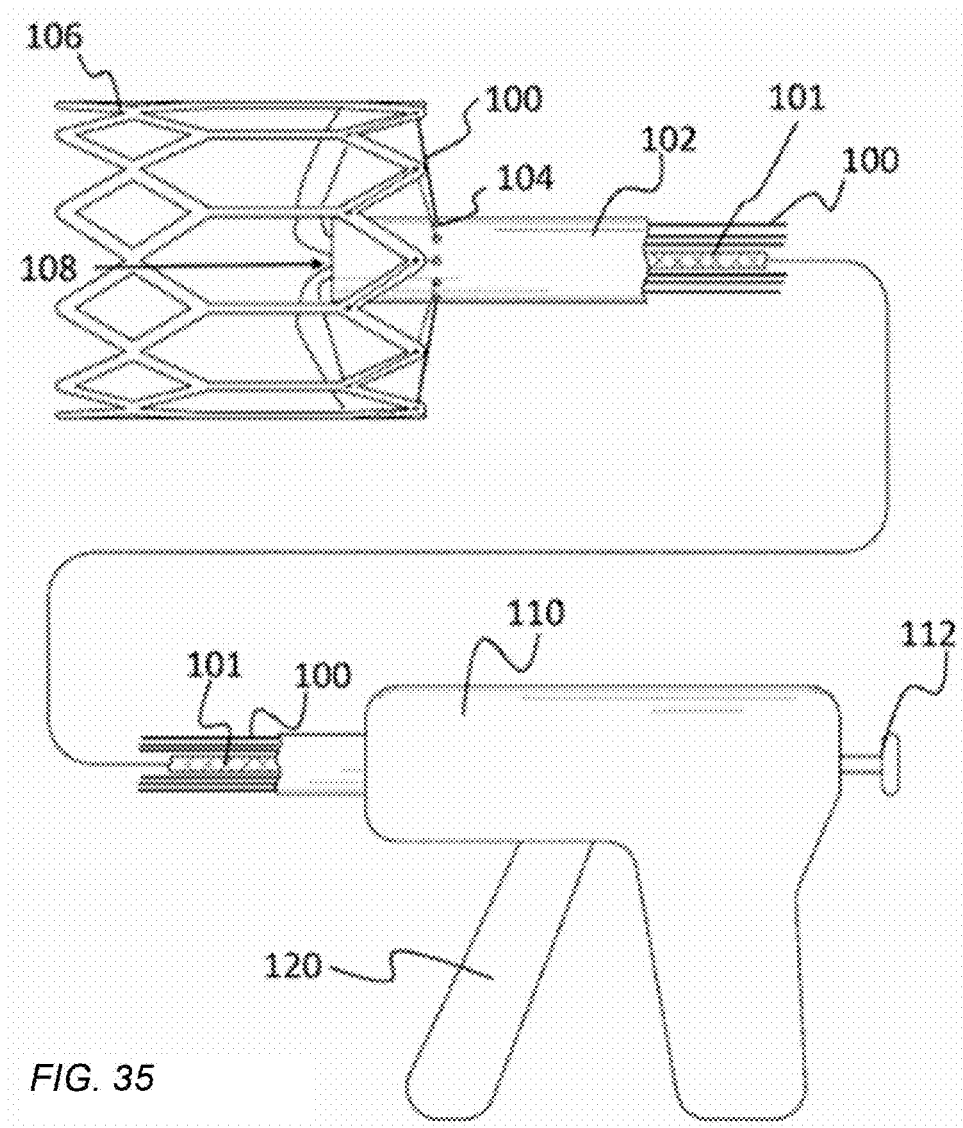
FIG. 35 is an illustration depicting draw lines extending substantially parallel with a release line and through a stent and to a delivery device.

As shown in FIG. 35, the stent delivery system includes a plurality of draw lines 100 (e.g., twelve lines or any other desired number) that extend from a handle 110 substantially parallel with a release line 101 (internal of a restraining part (i.e., glide 102)) and out of distal end 108 of glide 102, through a stent 106 and back through restraining holes 104 in the glide 102. Note that the delivery system includes a restraining part that is operable to selectively restrain the draw lines 100 during delivery. However, the restraining part also needs to be formed to allow the draw lines 100 to glide out of the said part and, as such, is hereinafter referred to as the glide 102.

The draw lines 100 in effect keep the stent 106 affixed with the glide 102 during delivery. They can also be selectively drawn (i.e., pulled) to turn the stent 106 as desired during delivery and implantation. The draw lines 100 can be free on their proximal ends, or desirably, connected with a draw line trigger 120 or other suitable component of the delivery device 110. The release line 101 is connected to a handle release trigger 112 or knob (or other suitable device for drawing the release line 101) of the delivery device 110. The draw lines 100 can be pulled to hold the stent 106 tight against the glide 102 during delivery. When at the desired delivery site, the release line 101 is pulled, which in turn releases the draw lines 100, allowing the draw lines 100 to be pulled out of the stent 106 and, thereby, release the stent 106 at the desired location These components are described in further detail below. It should be noted that the draw lines 100 can be formed of any material that allows for formation or fixation of an opening (an example of which described below with respect to the opening 200). As a non-limiting example, the draw lines 100 can be formed of monofilaments (e.g., nylon) that are pierced with a needle or other device to form an opening therethrough. FIG. 36A, for example, illustrates another non-limiting example of a draw line 100. In this example and as shown in FIG. 36A, one or more draw lines 100 are formed of a braided suture 201 to provided additional strength. To be contrasted with the example above where each draw line is a single monofilament, in this aspect, each draw lines is braided suture 201 formed of many filaments. For example, each braided suture 201 (i.e., draw line) is formed of any suitably braidable filaments, non-limiting examples of which include nylon, Polytetrafluoroethylene (PTFE), Ultra-high-molecular-weight polyethylene (UHMWPE), polyester, and Polyether ether ketone (PEEK). For further understanding, FIG. 36A is an illustration of the braided suture 201. FIG. 36B is an expanded view of FIG. 36A, showing the braided suture 201 as a three-strand braided structure formed of at least three strands 203. Further, FIG. 36C is an expanded view of FIG. 36B, illustrating multiple monofilaments 205 that are aliened to form each of the individual strands 203.

To provide the delivery and detachment features herein, the braided suture 201 includes at least one knot (and possibly multiple knots). For example and as shown in FIG. 36D, the braided suture 201 can be twisted into a first knot 114 (and additional knots as desired), a tightened version of which is shown in FIG. 36E. As can be appreciated by those skilled in the art, there are many techniques for tying a knot, one of which is illustrated in FIGS. 36D and 36E; however, the invention is not intended to be limited thereto as the knot(s) can be formed using any suitable technique, another non-limiting example of which is illustrated in FIGS. 37A through 37D.

Figure 36F:
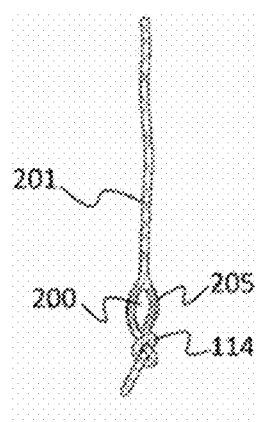
FIG. 36F is an illustration of an opening created in the braided suture by piercing between monofilaments, close to but proximal of the knot (as shown in FIG. 2E).

It is desirable that the suture knots are kept minimal in profile so that they pass freely through size constraining features (such as the restraining holes in the glide and the stent holes in the stent). It is also desirable that each braided suture is as uniformly pliable as practical so that the braided sutures slide freely through and around surfaces and edges (such as the stent). It is also desirable that the braided sutures and knot(s) provide adequate strength, e.g., to secure the stent (such as but not limited to a stented heart valve) in a collapsed state. A desired aspect is described in which the profile (size) of the suture knot(s) is/are kept minimal, in which changes to the braided suture pliability is minimalized, and in which the braided suture knots provide adequate strength. As a non-limiting example, the suture knot profile illustrated in FIGS. 36D, 36E, and 36F is approximately three times the braided suture profile, or, since the braided suture profile is approximately three times the strand profile, approximately nine times the strand profile.

In another aspect and as shown in FIG. 37B through 37E (and 38A through 28E, 39A and 39B), the knot profile(s) are approximately five times the strand profile. An objective of a desired embodiment of the knot/braid pattern is illustrated in FIGS. 37A through 37E is to maintain braided suture pliability with minimal profile and adequate strength.

As described in further detail below, to provide the draw and detachment features, the braided suture 201 needs an opening formed therethrough. FIG. 36F, for example, provides an illustration of an opening 200 created in the braided suture 201 by piercing between monofilaments 205. The opening 200 can be formed at any suitable location; however, desirably, the opening 200 is formed proximal to the first knot 114 with approximately half of the monofilaments 205 spread to each side of the opening 200.

Figures 37A, 37B:
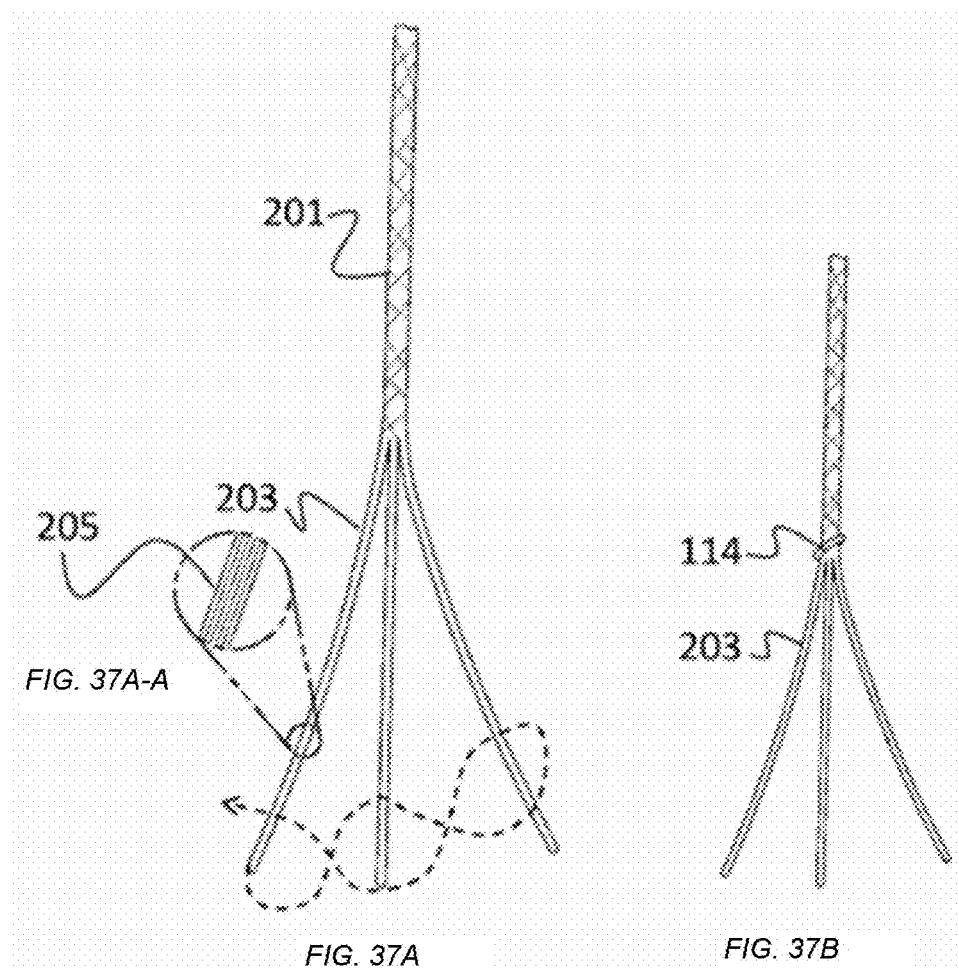
FIG. 37A is an illustration of a braided suture where the strands have been separated at one end.
FIG. 37B is an illustration of a knot formed by looping strand one around the other two strands and tying a knot close to the point at where the strands have been separated.
Figures 37C, 37D:
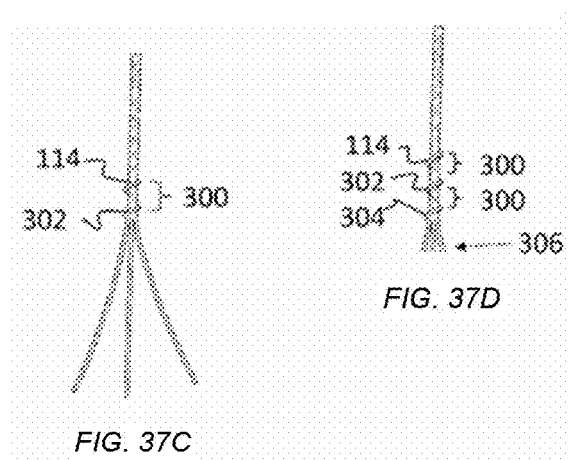
FIG. 37C is an illustration of braiding distal from the knot illustrated in FIG. 3B for a distance and then tying a second knot by looping strand two around the other two strands and tying a knot.
FIG. 37D is an illustration of braiding distal from the knot in FIG. 3C for a distance and then tying a third knot by looping strand three around the other two strands and tying a knot, further depicting the strands as being cut a short distance distal of the third knot.

As noted above, another example of a knot tying process is illustrated in FIGS. 37A through 37D. For example, FIG. 37A illustrates the braided suture 201 where the individual strands 203 have been separated at one end. As noted above and as illustrated in FIG. 37A-A (which is an expanded view of FIG. 37A), the individual strands 203 are formed of multiple mono-filaments 205. In this aspect and as shown in FIG. 37B, the knot is formed by looping a first strand around the other two strands and tying the knot 114 close to the point at where the strands 203 have been separated. After the first knot 114 is tied, it may be desirable to tie as few additional knots, as shown in FIGS. 37C and 37D. Thus, the strands can braided at the distal end for a desired distance 300 with a second knot 302 being tied, for example, by looping a second strand around the other two strands and tying the second knot 302. A desired distance 300 is the span of 4 or 5 braid crossings for one preferred embodiment but may be chosen differently to suit another aspect, which is important because this helps maintain suture pliability so that the braided sutures slide freely through and around surfaces and edges (such as the stent) while also providing adequate knot strength.

As noted above, any desired number of knots can be incorporated into the braided suture 201. However, desirably, three knots are included so that each of the three strands is knotted and each strand contributes to the overall strength. For example, FIG. 37D is an illustration of braiding the strands distal from the second knot 302 in FIG. 37C for a distance 300 and then tying a third knot 304 by looping a third strand around the other two strands and tying the third knot 304. In this non-limiting example, the strands are illustrated as being cut 306 a short distance distal of the third knot 304.

The braided suture 201 is less pliable at the knot(s) than in the braided lengths and less pliable at larger knots than at smaller knots. Thus, minimal knot size serves to minimize the change in braided suture pliability. The braided section between knots serves to spread the change in braided suture pliability over a length while simultaneously maintaining adequate knot slip strength. In other words, it is preferred that the discontinuity in pliability is smaller (in both scale and in physical length) and spread out in length rather than larger (in both scale and physical length). The triplicate knot pattern (as shown in FIG. 37D) secures each strand and provides adequate strength. In another aspect, the braided suture 201 is approximately the size of a human hair (i.e., in diameter or width), the strands are approximately one third the size of a human hair and the individual filaments are much smaller. Of course this is only illustrative and other knot/braid configurations are possible.

Figures 37E, 38A:
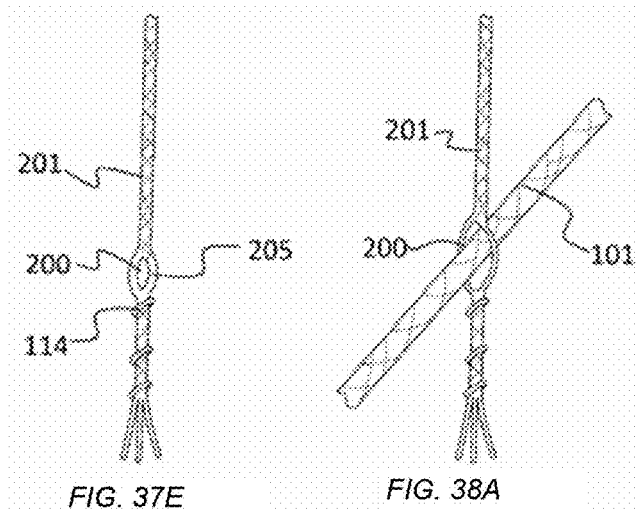
FIG. 37E is illustration of an opening created in the braided suture by piercing between monofilaments, close to but proximal of the first knot.
FIG. 38A is an illustration depicting positioning of a second, larger size suture (i.e., release line) through the opening of the braided suture depicted in FIG. 4E.
Figure 37B:
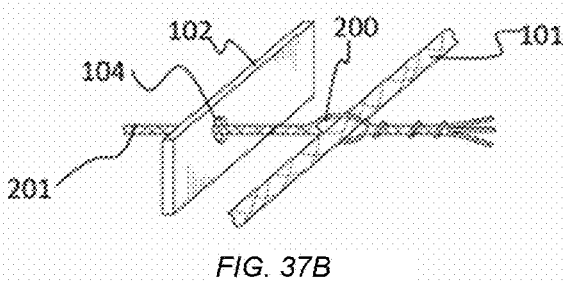

As was the case above and as shown in FIG. 37E, the opening 200 is created in the braided suture 201 by piercing between monofilaments 205, close to but proximal of the first knot 114. Desirably, approximately one half of the monofilaments are separated to each side of the opening 200. After the opening 200 is formed, the release line (depicted as element 101 in FIG. 35) is positioned through the opening 200.

For example and as shown in FIG. 38A, the release line 101 (e.g., a second, larger-size suture) is positioned through the opening 200 of the braided suture 201 structure. The release line 101 is formed of any suitably durable material, a non-limiting example of which includes nylon, UHMWPE, polyester suture, stainless steel wire, super elastic nitinol wire. As shown in FIG. 38B, the braided suture 201 and release line 101 are used in conjunction with a restraining part (e.g., the glide 102). The restraining part or glide 102 serves to provide a structure against which the release line 101 is restrained, thereby allowing a tensile force to be placed on the draw lines. As shown, the glide 102 includes at least one restraining hole 104 therethrough. The braided suture 201 passes through the restraining hole 104, with the larger release line 101 passing through the opening 200 of the braided suture 201. Notably, the diameter of the release line 101 may be greater than the restraining hole 104 in the glide 102 or the release line may be sufficiently stiff which prevents the release line 101 from being pulled through the restraining hole 104 when the braided suture 201 is being drawn taut.

Figure 38C:
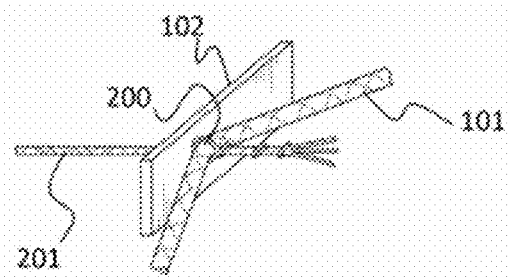
FIG. 38C is an illustration similar to that of FIG. 38B, depicting the braided suture under tension.
Figure 38D:
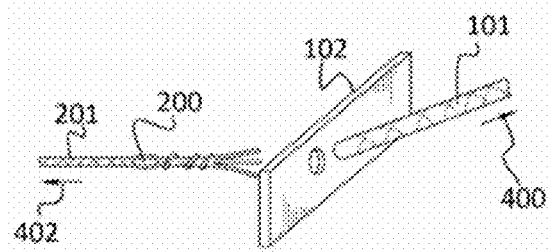
FIG. 38D is an illustration depicting the larger release line being pulled out of the braided suture, the braided suture (being under tension) slips out of the restraining part.
Figure 38E:
FIG. 38E is an illustration depicting collapse of the opening in the braided suture.

FIG. 38C is an illustration similar to that of FIG. 38B, depicting the braided suture 201 structure under tension when being pulled as a draw line. Notably, the stent is affixed with the glide 102 via the draw line (braided suture 201), with the braided suture 201 affixed within the glide 102 since the release line 101 is passing through the opening 200. When the stent is at the desired implant location, a user can pull on the release line 101 (using the delivery device). As shown in FIG. 38D, as the release line 101 is pulled 400 toward the delivery device, the release line 101 is pulled out of the opening 200 in the braided suture 201. With the release line 101 drawn from the opening 200, the braided suture 201 is free to be drawn 402 free of the glide 102 and, thereafter, drawn from the stent and back into the distal end of the glide 102. As can be appreciated by those skilled in the art and as shown in FIG. 38E, the opening 200 is easily collapsed (as depicted) to allow the suture 201 to be drawn from the glide and stent to allow for detachment from the stent.

Figures 39A, 39B:
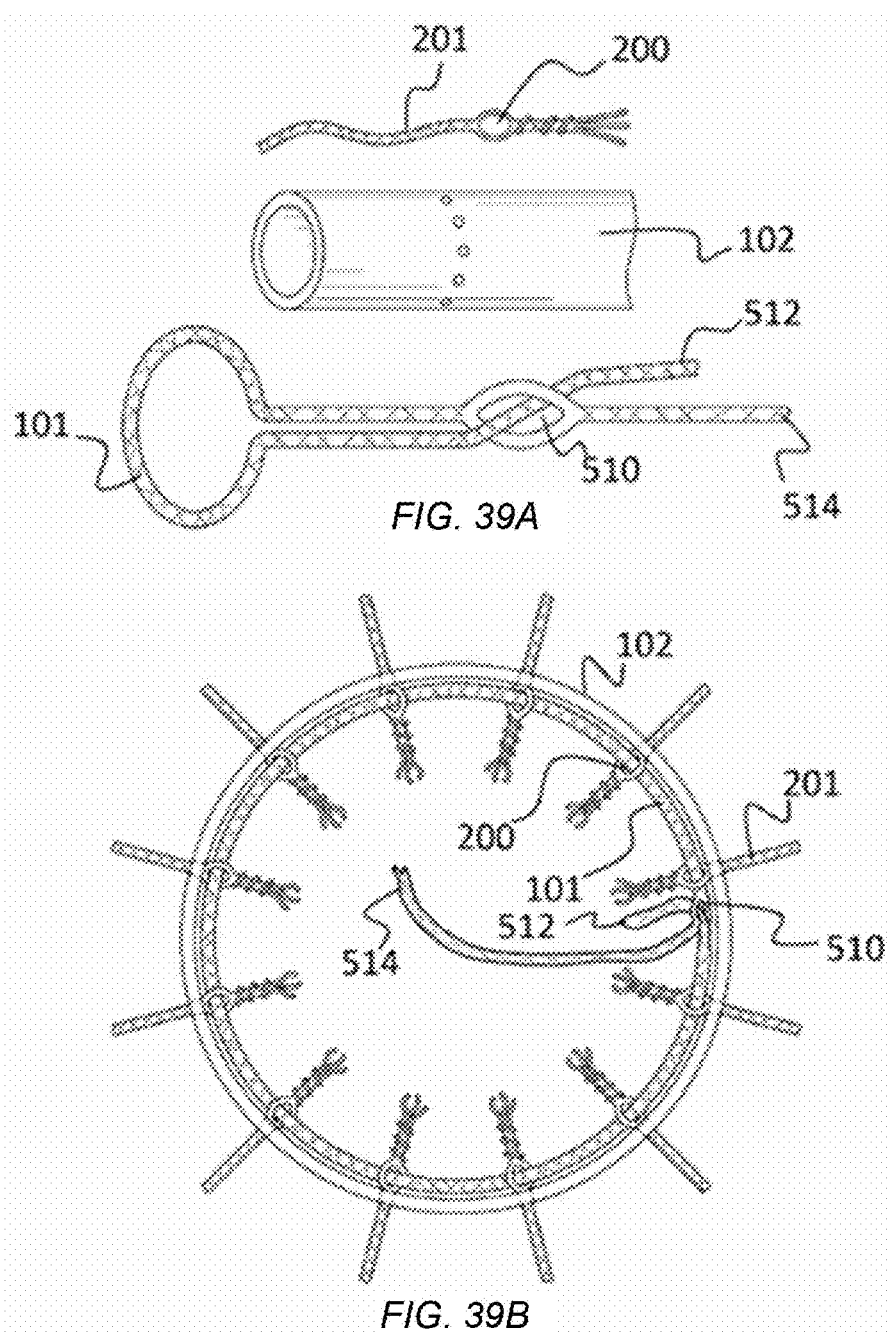
FIG. 39A is an illustration depicting components of the delivery system, including a draw line (e.g., braided suture), restraining part (i.e., glide), and larger suture (i.e., release line).
FIG. 39B is an illustration depicting a distal end-view, showing draw lines inserted through the glide, with a release line positioned through openings in the draw line.

Thus and as depicted in FIG. 39A, the delivery system includes at least a draw line (e.g., a plurality of braided suture(s) 201), a restraining part (e.g., a glide 102), and a larger suture (i.e., a release line 101). The release line 101, in one aspect, can be formed into include a release line opening 510 (e.g., by piercing the release line 101 or through any other suitable technique for forming an opening in a line). The release line 101 also includes a distal end 512 and a proximal end 514 that continues to the delivery device 110 (as shown in FIG. 35). The use of the release line opening 510 provides a technique for lightly fixing the distal end 512 of the release line 101 so that it does not inadvertently move out of the draw lines (e.g., braided sutures 201) prematurely. When pulling the proximal end 514 of the release line 101 (via the handle release trigger), the distal end 512 of the release line 101 slides out of the release line opening 510 and then out of the braided suture openings 200.

As noted above and as further illustrated in the distal-end view of FIG. 39B, the braided sutures 201 are affixed with the glide 102 by the release line 101 which passes through openings 200 in the braided sutures 201. Also as shown, the distal end 512 of the release line 101 is passed through the release line opening 510, with the proximal end 514 of the release line 101 passing through the glide 102 and toward the delivery device.

Figure 39C:
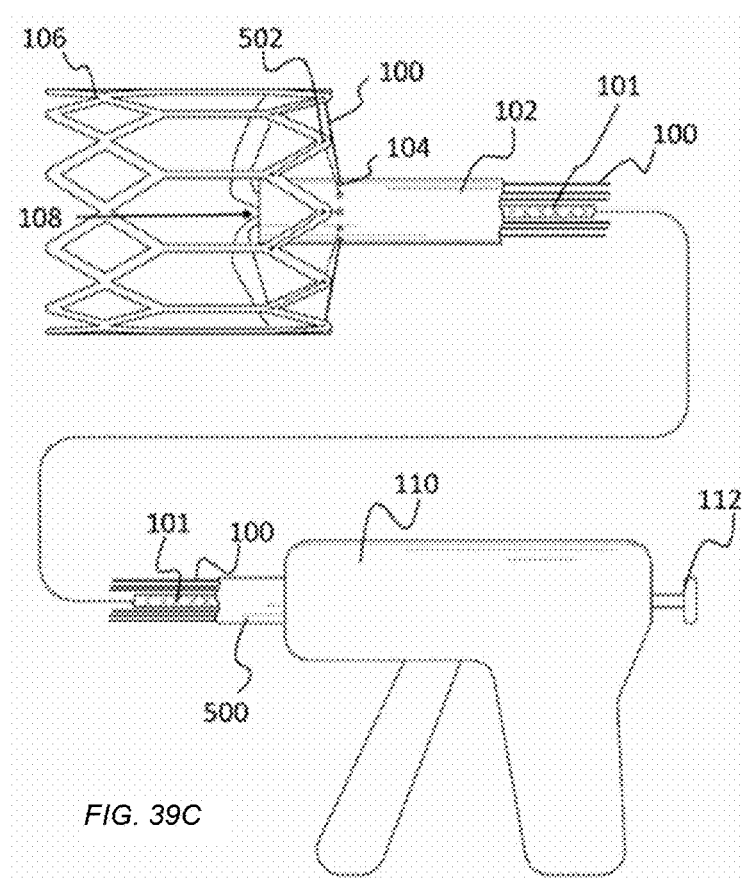
FIG. 39C is an illustration depicting draw lines extending substantially parallel with a release line and through a stent and to a delivery device.

For clarity, the delivery system described herein can be implemented with any suitable stent delivery device 110, a non-limiting example of which is shown in FIG. 39C. A non-limiting example of an off the shelf delivery device is that sold by Edwards Lifesciences Corporation, and Medtronic CoreValve®. The glide 102 (i.e., restraining party can be used in conjunction with the sheath 500 of such a delivery device 110. Also projecting from the delivery device 110 are the draw lines 100 (e.g., braided sutures 201) and release line 101. For clarity and as noted above, the braided sutures 201 are provided as a non-limiting example of suitable draw lines 100 according to the principles of the present invention and, as such, are terms that are used herein interchangeably. The draw lines 100 continue through the glide 102 and out of the distal end 108 of the glide 102. The glide 102 is any suitable device that is operable for restraining the draw lines 100 as described. For example, the glide 102 is a cylindrically-shaped barrel or tube. The draw lines 100 continue out of the glide 108 and through the various stem holes 502 in the stent 106. After passing through one or more stent holes 502 in the stent 106, the draw lines 100 continue through restraining holes 104 in the glide 102 and back into the glide 102. Inside the glide 102 (as shown in FIG. 39B), the draw lines 100 are affixed within the glide 102 due to the release line 101 passing through the openings 200 in the draw lines 100 (i.e., braided sutures 201). When a user pulls the release line 101 with the delivery device 110, the release line 101 is pulled out of the openings 200 in the draw lines 100, which allows the draw lines 100 to be pulled out of the restraining holes 104 in the glide 102 and, also, out of the stent holes 502 in the stem 106, thereby detaching entirely from the stent 106.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method for positioning or repositioning a transcatheter heart valve at a target site in a heart of a subject comprising:
    a) providing an integrated ultrasound guided delivery system comprising:
        (i) a delivery catheter coupled to the transcatheter heart valve, and
        (ii) an intravascular ultrasound (IVUS) catheter operably coupled to the delivery catheter, wherein the IVUS catheter comprises an ultrasound transducer tip that is aligned with a base of leaflets of the transcatheter heart valve;
    b) advancing the transcatheter heart valve, via the delivery catheter, in the vicinity of a native valve at the aortic root of the heart,
    c) visualizing the native valve and the target site in real-time with pull-back imaging by the IVUS catheter, wherein visualizing the native valve further comprises visualizing calcification on the native valve at the target site, wherein the pull-back imaging provides real-time two-dimensional cross-sectional images or three-dimensional images of the aortic root and calcified spots on the native valve; and
    d) deploying the transcatheter heart valve at the target site, via the delivery catheter, based on the determination of a pattern of calcification on the native valve at the target site, aiming to maintain a conformal placement within the native valve annulus, thereby avoiding or minimizing paravalvular leak.

2. The method according to claim 1 comprising approaching to reach the heart through a vascular system.

3. The method according to claim 1 comprising approaching to reach the heart directly by poking the heart.

4. The method according to claim 1, further comprising producing a stack of cross-sectional images while retracting the IVUS catheter relative to the native valve, and tomographically combining the images to produce a three-dimensional representation of the aortic root.

5. The method of claim 1, wherein the target site is viewed while the ultrasound transducer tip is positioned distally past a distal terminus of the transcatheter heart valve or wherein the target site is viewed while the ultrasound transducer tip is positioned within the transcatheter heart valve.

6. The method of claim 1, wherein deploying the transcatheter heart valve at the target site comprises simultaneously viewing the target site and the transcatheter heart valve using the IVUS catheter.

7. The method of claim 1, wherein viewing the native valve and the target site comprises displaying the real-time images on a display.

8. The method of claim 1, wherein deploying the transcatheter heart valve to the target site comprises radially expanding the transcatheter heart valve.

9. The method of claim 8, further comprising: radially compressing the transcatheter heart valve; repositioning the delivery catheter with respect to the target site while viewing the target site with the with the IVUS catheter; and redeploying the transcatheter heart valve while viewing the transcatheter heart valve and the target site with the IVUS catheter.

10. The method of claim 1, wherein the IVUS catheter is rotated and moved distally or proximally while imaging.

11. The method of claim 1, performed without a second imaging modality.

12. The method of claim 1, wherein the target site comprises an aortic annulus and the transcatheter heart valve is a prosthetic aortic heart valve.

13. The method of claim 1, wherein deploying the transcatheter heart valve comprises positioning or repositioning the transcatheter heart valve in six degrees of freedom.

14. The method of claim 1, wherein the ultrasound transducer tip is positioned such that annular diameters of a native valve can be imaged and measured.

15. The method of claim 1, wherein the delivery catheter is 24 French (Fr) or less in size.

16. The method of claim 1, wherein the system is additionally equipped with an optical computed tomography (OCT) sensor.

17. The method of claim 1, wherein the transcatheter valve is selected from the group consisting of an aortic valve, a mitral valve, a pulmonary valve, and a tricuspid valve.

\* \* \* \* \*